United States Patent
Villette et al.

(10) Patent No.: US 10,473,603 B2
(45) Date of Patent: Nov. 12, 2019

(54) APPARATUS, SYSTEM AND METHOD FOR INSPECTING COMPOSITE STRUCTURES USING QUANTITATIVE INFRA-RED THERMOGRAPHY

(71) Applicant: Saudi Arabian Oil Company, Dhahran (SA)

(72) Inventors: Thibault Villette, Al-Khobar (SA); Abderrazak Traidia, Dhahran (SA); Ayman Amer, Thuwal (SA); Fadl Abdellatif, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 174 days.

(21) Appl. No.: 15/490,578

(22) Filed: Apr. 18, 2017

(65) Prior Publication Data
US 2018/0299392 A1    Oct. 18, 2018

(51) Int. Cl.
*G01N 25/72*    (2006.01)
*G01N 17/00*    (2006.01)
(Continued)

(52) U.S. Cl.
CPC .............. *G01N 25/72* (2013.01); *H04N 5/33* (2013.01)

(58) Field of Classification Search
USPC ............................... 374/5, 57, 121, 124, 208
See application file for complete search history.

(56) References Cited

U.S. PATENT DOCUMENTS

| 4,647,220 A | * | 3/1987 | Adams | G01N 25/72 |
| | | | | 250/330 |
| 4,854,724 A | * | 8/1989 | Adams | G01N 25/72 |
| | | | | 374/5 |

(Continued)

FOREIGN PATENT DOCUMENTS

CN    103487443 A    1/2014

OTHER PUBLICATIONS

Saintey M B, et al., "An artificial neural network interpreter for transient thermography image data", NDT & E International, Butterworth-Heinemann, Oxford, GB, vol. 30, No. 5, Oct. 1997, pp. 291-295.

(Continued)

*Primary Examiner* — Mirellys Jagan
(74) *Attorney, Agent, or Firm* — Leason Ellis LLP

(57) ABSTRACT

A system and method for inspecting a surface of a structure for defects includes an inspection apparatus having a heating device for heating a section of the surface of the structure, an infrared camera for receiving infrared radiation from the surface in response to heating, a controller configured to generate thermographs from the received infrared radiation, and a communication device. A training system includes an expert system module configured to determine correlations between a set of thermographs generated by a thermal simulation of modeled structural elements with defects, and parameters of the modeled structural elements. A computer system communicatively coupled to the training system and the inspection apparatus, is adapted to receive thermographs received from the inspection apparatus and to detect quantitative parameters of defects in the structure using the correlations obtained from the training system.

16 Claims, 15 Drawing Sheets

(51) Int. Cl.
*G01J 5/00* (2006.01)
*G01K 1/00* (2006.01)
*H04N 5/33* (2006.01)

(56) References Cited

U.S. PATENT DOCUMENTS

| | | | | |
|---|---|---|---|---|
| 5,631,465 | A | * | 5/1997 | Shepard .............. G01N 25/72 250/330 |
| 5,963,030 | A | | 10/1999 | Stark |
| 7,064,332 | B2 | | 6/2006 | Favro et al. |
| 7,885,381 | B2 | | 2/2011 | Nagumo et al. |
| 8,166,823 | B2 | | 5/2012 | Lam et al. |
| 8,184,281 | B2 | | 5/2012 | Engelbart et al. |
| 8,577,120 | B1 | | 11/2013 | Koshti |
| 8,721,077 | B2 | | 5/2014 | Vermeer et al. |
| 8,759,780 | B2 | | 6/2014 | Dobbs |
| 9,534,958 | B1 | * | 1/2017 | Lhamon .............. G01J 5/0025 |
| 2001/0042834 | A1 | | 11/2001 | Kenway |
| 2003/0055594 | A1 | * | 3/2003 | Bunker .............. G01K 11/30 702/134 |
| 2003/0137318 | A1 | | 7/2003 | Enachescu et al. |
| 2004/0028113 | A1 | * | 2/2004 | Schlagheck ........ G01N 25/72 374/57 |
| 2004/0159790 | A1 | | 8/2004 | Thompson et al. |
| 2006/0191622 | A1 | | 8/2006 | Ritter et al. |
| 2006/0222237 | A1 | | 10/2006 | Du et al. |
| 2009/0245321 | A1 | | 10/2009 | Ringermacher et al. |
| 2012/0201347 | A1 | | 8/2012 | Prentice et al. |
| 2014/0022380 | A1 | | 1/2014 | Nissen et al. |
| 2015/0083920 | A1 | * | 3/2015 | Shepard .............. G01J 5/0205 250/341.6 |

OTHER PUBLICATIONS

Clemente Ibarra-Castanedo, et al., "Thermographic nondestructive evaluation: overview of recent progress", Proceedings of SPIE, vol. 5073, Apr. 3, 2003.

Darabi, et al., "Neural network based defect detection and depth estimation in TNDE", NDT& E International, Butterworth-Heinemann, Oxford, GB, vol. 35, No. 3, Apr. 2002.

Rudi Heriansyah, et al., "Defect Depth Estimation in Passive Thermography using Neural Network Paradigm" 6th WSEAS International Conference on Circuits, Systems, Electronics, Control & Signal Processing, Dec. 31, 2007.

G. K. Vijayaraghavan, et al., "Estimating Parameters of Delaminations in GRP Pipes Using Therman NDE and ANN", AIP Conference Proceedings, 2010, pp. 350-355.

Galietti, U. et al, "Defect Detection in Composite Materials by Thermography and Neural Networks" SEM X International Congress & Exposition on Experimental & Applied Mechanics (2004).

Dudzik, S., "Characterization of Material Defects Using Active Thermography and an Artificial Neural Network" in Metrology and Measurement Systems, No. 3 (2013).

Péronnet, E. et al, "Non destructive Investigation of Defects in Composite Structures by Three infrared Thermographic Techniques", in International conference on experimental mechanics ICEM Jul. 15, 2012.

Thajeel, H., "Numerical modeling of infrared thermography techniques via ANSYS" Masters Theses. Paper 7344 (2013).

Marani, R. et al, "Automatic detection of subsurface defects in composite materials using thermography and unsupervised machine learning" in IEEE 8th International Conference on Intelligent Systems (2016).

Gao, B. et al, "Electromagnetic Thermography Nondestructive Evaluation:Physics-based Modeling and Pattern Mining" in Scientific Reports 6:25480 (2016).

Venegas, P., et al, "Image and Data Processing Techniques Applied to Infrared Thermographic Non-Destructive Inspections of Aeronautical Composite Components" in 4th International Symposium on NDT in Aerospace (2012).

Redmer, B. et al, "X-Ray Testing of Circumferential Welds by a Mechanized radiometric Weld Inspection System" in 2nd International Conference on MDE in Relation to Structural Integrity for Nuclear and Pressurized Components Aug. (2000).

* cited by examiner

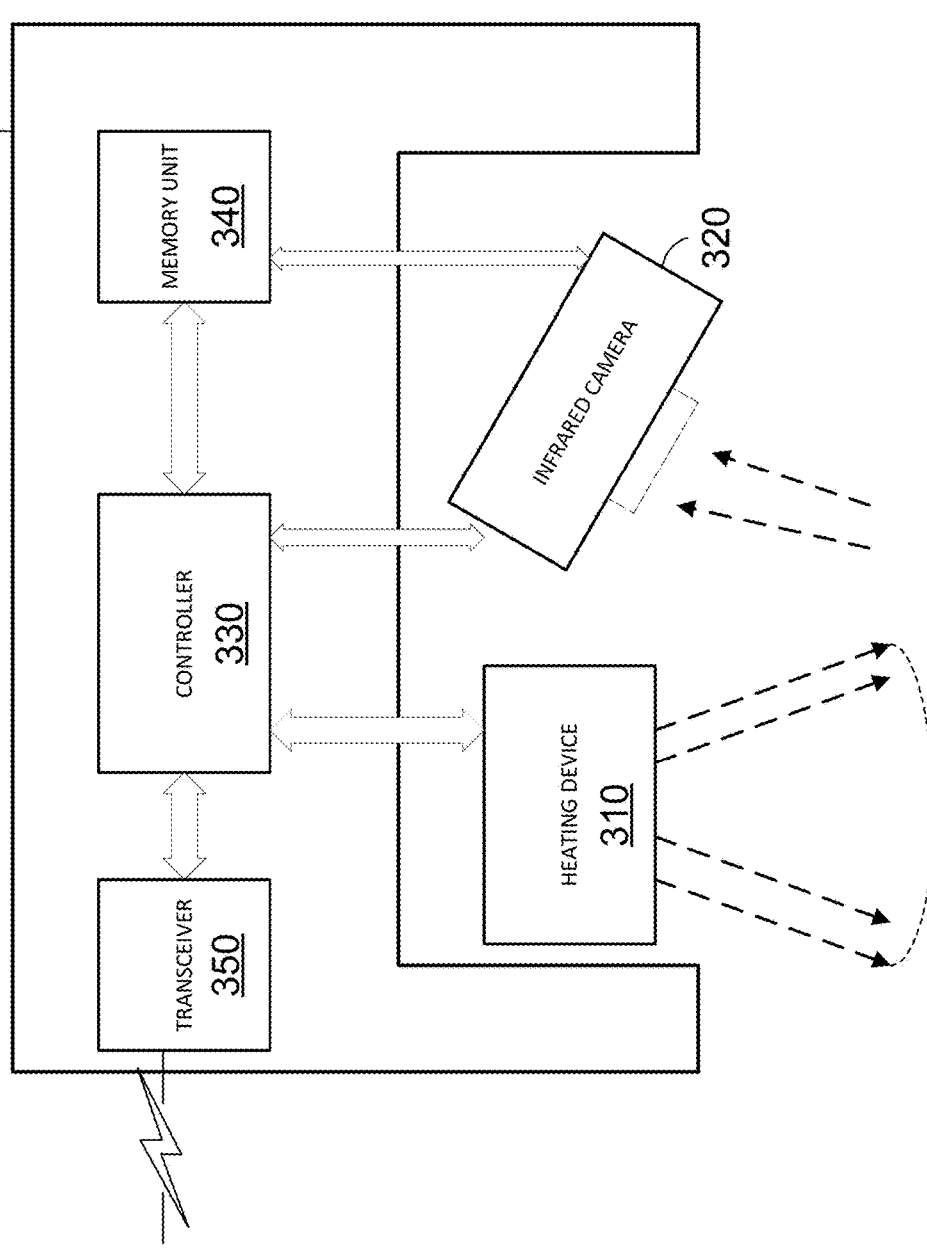

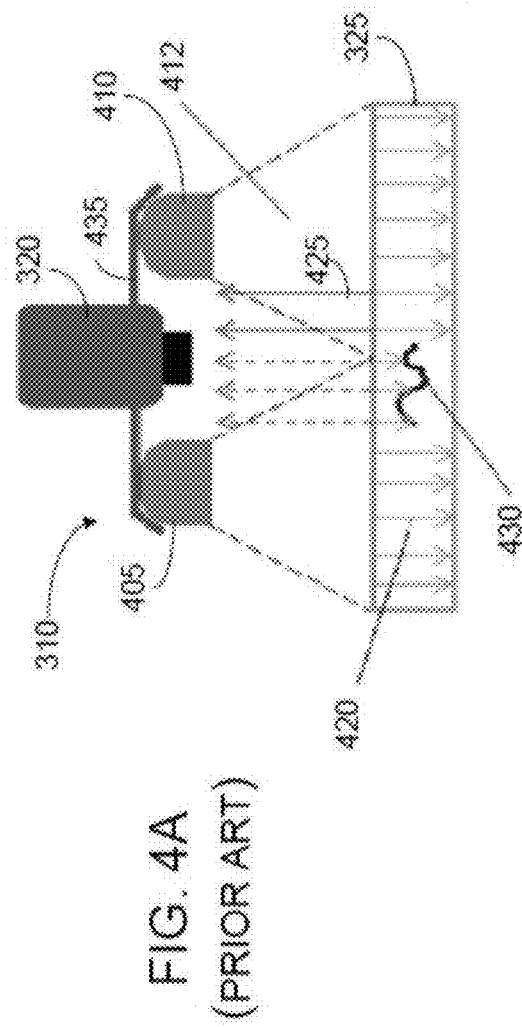
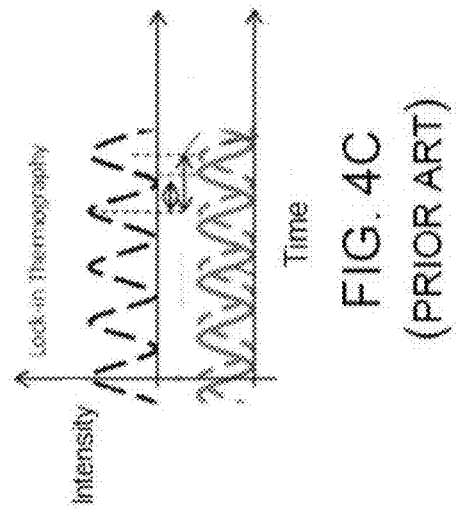
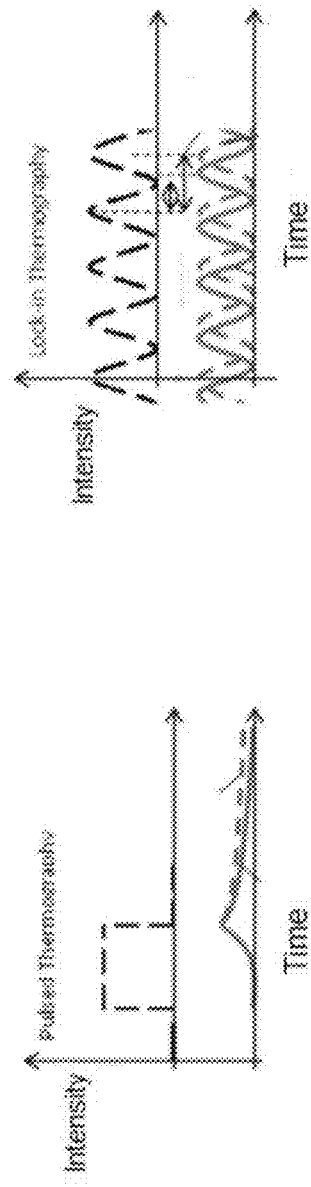
FIG. 4A (PRIOR ART)
FIG. 4B (PRIOR ART)
FIG. 4C (PRIOR ART)

$a_k$ defect first dimension,
$b_k$ defect second dimension
$c_k$ defect third dimension
$z_k$ out-of-plane coordinate of defect centroid
$\theta_k$ and $\varphi_k$ angles with inspection plane
$D_k$ class of defect e.g. delamination
$M_k$ media entrapped e.g. air

APPARATUS, SYSTEM AND METHOD FOR INSPECTING COMPOSITE STRUCTURES USING QUANTITATIVE INFRA-RED THERMOGRAPHY

FIELD OF THE INVENTION

The present invention relates to material inspection and characterization and in particular relates to an apparatus, system and method for inspecting composite structures using quantitative infra-red thermography.

BACKGROUND OF THE INVENTION

Composite materials (hereinafter "composites") are currently used as a replacement for metallic materials in many industrial applications because of their resistance to corrosion. In the oil and gas industry for instance, composites are used in filament wound composite structures such as pipes and vessel tanks. A pipeline made from composites is shown in FIG. 14 to indicate the scale of composite structures currently used in the field. While the benefits of corrosion resistance favor their use, composites can suffer from susceptibility to other types of damage such as impact, creep and aging.

Given the susceptibilities of composites to certain types of damage, it is important to periodically inspect composites to test whether such damage has occurred or is accumulating. It is also a requirement for the inspection to be non-destructive because it is infeasible to employ invasive techniques that interrupt the continued operation of the structures in the field. Suitable non-destructive testing (NDT) techniques should be able to accurately detect typical defects in composites, be easy to apply, and permit rapid and automated inspection of large areas. It would also be advantageous for such techniques to provide in-service inspection with minimum surface preparation.

Among common NDT techniques, infrared thermography stands out as a good candidate since it provides contact-free measurement (no need for coupling media), global and focused area scans, fast acquisition, and easy operation. Limitations of the sensitivity of infrared thermography equipment have until now restricted this technique to qualitative and boundary inspections, both of which are unable to provide accurate defect size, depth data or data on the nature of any entrapped media, and are limited to detecting defects located close to the surfaces of the inspected structures.

There is therefore a need for non-destructive techniques for rapidly, reliably and cost-efficiently inspecting composite structures in an accurate quantitative manner. The present invention is addressed to this and related needs.

SUMMARY OF THE INVENTION

According to an aspect of the present invention, a system for inspecting a surface of a structure for defects is provided. According to one embodiment, the system comprises: 1) an inspection apparatus including a heating device for heating a section of the surface of the structure, an infrared camera for receiving infrared radiation from the surface in response to heating, a controller configured to generate thermographs from the received infrared radiation, and a communication device; 2) a training system including an expert system module configured to determine correlations between a set of thermographs, the thermographs being generated by a thermal simulation of modeled structural elements with defects, and to determine parameters of the modeled structural elements; and 3) a computer system communicatively coupled to the training system and the inspection apparatus, the computer system adapted to receive thermographs received from the inspection apparatus and to detect quantitative parameters of defects in the structure using the correlations obtained from the training system.

In some embodiments, the structure is composed of a composite material. In some implementations, the quantitative parameters detected by the computer system include a location, a depth, an orientation, a defect type, an entrapped media type, or a sub-combination thereof. In further implementations, the expert system module employs an expert system (e.g., a neural network) to determine the correlations between the set of thermographs and the corresponding set of modeled structural elements. In still further embodiments, a combination of the foregoing can include a composite material as the structure, with the quantitative parameters detected by the computer system including a location, a depth, an orientation, a defect type and an entrapped media type, and in still further embodiments this combination can be implemented together with an expert module that employs a neural network as just described.

In some embodiments, the training system further includes a defect microstructure database module configured to generate the set of modeled structural elements, each structural element including an integrated defect. In some implementations, the training system also includes a virtual thermograph database module configured to perform a thermal analysis of each of the modeled structural elements and to generate transient thermographs corresponding to the structural elements. The thermal analysis can be implemented using finite element analysis. Again, embodiments can be implemented with each or all of the features noted in this paragraph.

In some implementations, the parameters of each of the modeled structural elements include location, orientation, defect type, defect size and entrapped media. The modeled defect type can be one of delamination, unique void, matrix cracking, fiber-matrix de-bonding, multiple voids, and holes. The modeled entrapped media can be one of liquid or gas.

In further embodiments of the present invention, the training system includes an optimized acquisition parameter module configured to automatically determine acquisition parameters for controlling the inspection apparatus based on material properties of the structure, environmental conditions, and a thermal analysis of a modeled structural element. In some implementations, the acquisition parameters determined by the optimized acquisition parameter module include a heating time, target heat flux level for operating the heating device, an acquisition time for operating the infrared camera of the inspection apparatus, or a sub-combination of these features. The thermal analysis can be performed on a modeled structural element having at least one of a smallest and a deepest defect.

In some implementations of the present invention, the computer system receives the acquisition parameters from the training system. In such implementations, the computer system transmits the acquisition parameters to the inspection apparatus. In further implementations, the expert system module employs a neural network to determine the correlations between the set of thermographs and the corresponding set of modeled structural elements.

According to another embodiment, the inspection apparatus includes a clamp element for fixing the apparatus to the surface of the structure, and a chassis unit for housing the heating element and infrared camera. In some implementations, the chassis unit is slidingly coupled to the clamp element and rotatable circumferentially with respect to the surface of the structure. In further implementations, the chassis unit and clamp element are coupled to rotatable and translatable wheels, thereby enabling the inspection apparatus to rotate circumferentially and translate longitudinally along the surface of the structure. For instance, the chassis unit and clamp element can be coupled to a robotic vehicle.

According to another aspect of the present invention, a system for inspecting a surface of a structure for defects comprises: 1) an inspection apparatus including a heating device for heating a section of the surface of the structure, an infrared camera for receiving infrared radiation from the surface in response to heating, a controller configured to generate thermographs from the received infrared radiation, and a communication device; 2), a training system including an expert system module configured to determine correlations between a set of thermographs and parameters of modeled structural elements, and an optimized acquisition parameter module configured to automatically determine parameters for controlling the inspection apparatus based on material properties of the structure and environmental conditions; and 3) a computer system communicatively coupled to the training system and the inspection apparatus, the computer system being adapted to receive thermographs received from the inspection apparatus and to detect quantitative parameters of defects including an entrapped media type in the structure using the correlations obtained from the training system.

According to still another aspect, a method of training a system to enable an inspection apparatus to perform an accurate quantitative inspection of a surface of a structure for defects is provided. In one embodiment in accordance with this aspect, the method comprises receiving operator inputs concerning properties of the structure and environmental conditions at the structure, generating a set of structural elements using the operator inputs, each of the modeled structural elements including an integrated defect, generating thermographs corresponding to each of the structural elements through application of a transient thermal analysis, and computing correlations between the thermographs and the parameters of corresponding structural elements, wherein the correlations enable thermographs taken of structures to be analyzed to determine quantitative parameters of defects in the structure. In some embodiments, the structure is composed of a composite material.

In some embodiments of the present invention, the transient thermal analysis employs finite element analysis. In other embodiments, the generated structural elements are characterized by a location, orientation, defect type, defect size, entrapped media, or a sub-combination thereof. In some implementations the defect type is one of delamination, unique void, matrix cracking, fiber-matrix de-bonding, multiple voids, and holes. The entrapped media can be a liquid or gas such as air, water and oil.

In further embodiments, the method includes determining optimal acquisition parameters for controlling the inspection apparatus based on material properties of the structure, environmental conditions, and a thermal analysis of a structural element. In some implementations, the acquisition parameters include a heating time, a target heat flux level, an acquisition time for operating the inspection apparatus, or a sub-combination of the foregoing. The thermal analysis can be performed on a structural element having at least one of a smallest and a deepest defect.

In some implementations, the correlations between the thermographs and the parameters of corresponding structural elements are determined using a machine learning technique. In more particular implementations, the machine learning technique employs a neural network.

According to yet another aspect of the present invention, a method of quantitatively inspecting a surface of a structure for defects, from which infrared thermographs are acquired by an inspection apparatus, is provided. One method in accordance with this aspect comprises obtaining a set of correlations between parameters of modeled structural defects and simulated thermographs of the modeled structural defects, and optimal acquisition parameters for configuring the inspection apparatus for acquiring thermograph data from the structure, communicating the acquisition parameters to the inspection apparatus, receiving infrared thermograph data acquired from the structure from the inspection apparatus, analyzing the received thermograph data using the obtained correlations, and determining parameters of defects within the structure based on the analysis of the received thermograph.

In some embodiments of the method, acquisition parameters are communicated to the inspection apparatus. In some embodiments, thermograph data is received from the inspection apparatus via wireless communication. In some embodiments, the parameters of defects within the structure that are determined include a location, a depth, an orientation, a defect type, an entrapped media type, or a sub-combination of the foregoing. In further embodiments, the acquisition parameters for configuration the inspection apparatus include a heating time, a target heat flux level for applying heat to the structure, an acquisition time detecting infrared radiation from the structure, or a sub-combination thereof. The optimal acquisition parameters can be determined based on a material of the structure and environmental conditions at the structure. More particular embodiments include a combination of the features described in this paragraph.

According to yet another aspect of the present invention, a method of quantitatively inspecting a surface of a structure using an inspection apparatus having a heating device and an infrared camera is provided. One method in accordance with this aspect comprises receiving optimal acquisition parameters for configuring the heating element, heating a section of the structure using the heating device according to the received acquisition parameters, detecting infrared radiation emitted from the section of the structure according to the received acquisition parameters, generating thermograph data from the detected infrared radiation, and communicating the thermograph data to a computer system to determine defects of the structure using the thermograph data. The analysis employs a set of correlations between parameters of modeled structural defects and simulated thermographs of the modeled structural defects and obtains parameters of corresponding to the received thermograph data using the correlations.

In some embodiments, the method further includes removably fixing the inspection apparatus in proximity to the structure using a clamp element. In some implementations, the method includes rotating the heating device and infrared camera of the inspection apparatus circumferentially around the structure with respect to the clamp element and can also include translating the clamp element longitudinally over the structure using at least one wheel. The acquisition parameters can include a heating time, a target heat flux level for heating the section of the structure, an acquisition time detecting infrared radiation from the structure, or a sub-combination thereof. In some implementations, the optimal acquisition parameters are determined based on a material of the structure, the environmental conditions at the structure, or both.

According to yet another aspect of the present invention, an apparatus for inspecting a surface of a structure for defects is provided. One embodiment of an apparatus according to this aspect of the comprises: 1) a clamp element for removably fixing the apparatus in proximity to the surface of the structure; and 2) a chassis unit coupled to the clamp element, the chassis unit housing: i) a heating device configurable to heat a section of the surface of the structure; ii) an infrared camera configurable to acquire infrared radiation from the surface of the structure; iii) a controller communicatively coupled to and operative to control the heating device and infrared camera; and iv) a transceiver. The controller receives optimal acquisition parameters from a system that determines the parameters based on a material of the structure and environmental conditions in a proximity of the structure.

In some embodiments, the inspection apparatus further comprises sliding elements coupled between the chassis unit and the clamp element that enable the chassis unit to rotate along the clamp element circumferentially around the structure. In other embodiments, the inspection apparatus further comprises rotatable and translatable wheels fixed to ends of the clamp element and chassis unit, the wheels enabling the clamp element and chassis unit to rotate circumferentially and translate longitudinal over the surface of the structure. In some implementations, the optimal acquisition parameters include a heating time, a target flux level for applying heat the section of the structure using the heating device, an acquisition time detecting infrared radiation from the structure using the infrared camera, or a sub-combination thereof.

These and other aspects, features, and advantages can be appreciated from the following description of certain embodiments of the invention and the accompanying drawing figures and claims.

BRIEF DESCRIPTION OF THE DRAWINGS

FIG. 3 is a schematic diagram showing the components of an inspection unit (chassis) of the inspection apparatus according to an exemplary embodiment of the present invention.

FIG. 4A is a schematic diagram of an embodiment of a heating device and infrared camera that can be employed in an inspection apparatus according to the present invention.

FIG. 4B is a graph showing exemplary activation input (above) and infrared responses (bottom) according to a pulse thermography activation.

FIG. 4C is a graph showing exemplary activation input (above) and infrared responses (bottom) according to a lock-in thermography activation.

DETAILED DESCRIPTION OF CERTAIN EMBODIMENTS OF THE INVENTION

A systematic approach to reliably and quantitatively inspecting structures using infrared thermography is disclosed. The approaches disclosed herein are particularly applicable for inspecting composite materials. In some embodiments, the inspection system includes three distinct elements: 1) a training system that a) models structural defects of a composite material, b) performs a mathematical simulation of how the modeled defects react to heating and which generates virtual thermographs (images indicative of temperature) showing temperature changes of the modeled defects over time, and c) correlates the virtual thermographs with parameters of the modeled defects using a machine learning approach, producing an accessible virtual thermograph database; 2) an inspection apparatus that is used at the site of the structure, and that includes a heating element to apply heat to a section of the structure surface, and a recording device to record infrared radiation emitted from the heated section of the surface; and 3) an onsite computing system that: a) accesses the training system to obtain the correlations between the thermographs of the parameters of the defects; b) receives thermographs of recorded infrared radiation from the inspection apparatus; and c) quantitatively determines the parameters of the received thermograph using the correlations obtained from the training system. Additional details of the system are discussed in reference to the illustrated embodiments.

The disclosed system provides an integrated solution to the problem of detecting defects over composite structures with large and/or extended surfaces that is easy to implement, provides for fast inspection, and is economically efficient.

As a preliminary matter, the terms "thermograph" and "thermogram" are interchangeable herein and both are to be interpreted as images of a surface area captured by an infrared camera or sensor in which a color, hue, gray scale or other differentiating mark indicates a specific temperature or temperature range.

Inspection System

Figure 1:
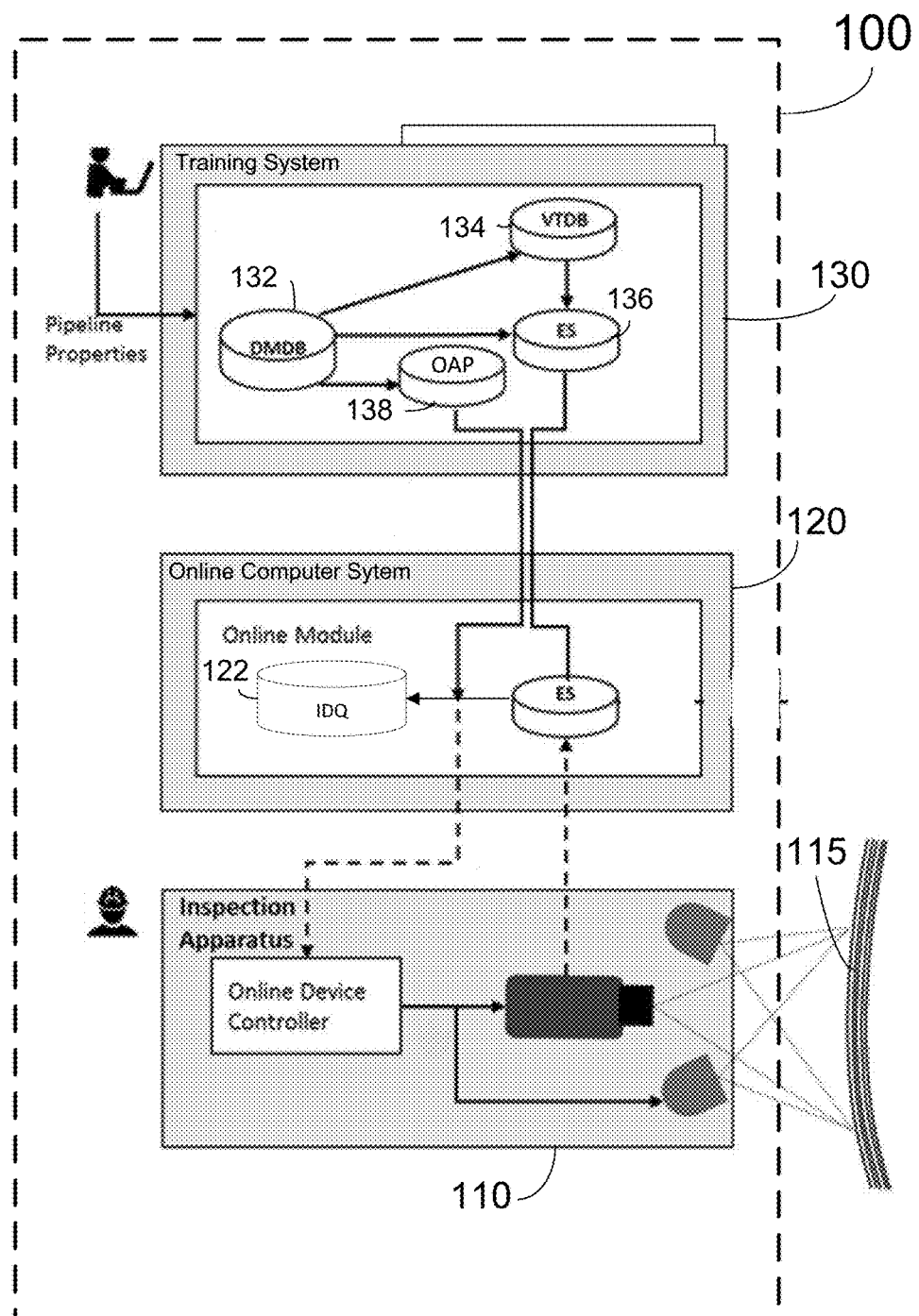
FIG. 1 is a schematic diagram of a system for inspecting composite structures using quantitative infrared thermography according to an exemplary embodiment of the present invention.

Turning to FIG. 1, an embodiment of a system 100 for inspecting composite structures using quantitate infrared thermography is shown. The system 100 includes an inspection apparatus 110 that is positioned proximate to a surface section 115 of a structure, which can be made of a composite. The apparatus, described in greater detail below, heats the surface section 115 and detects and records infrared radiation that is emitted from the section 115 in response to being heated. The inspection apparatus 110 is communicatively coupled, preferably wirelessly, but optionally by a wired connection, to a computer system 120. Computer system 120 is operable to receive and process the data recorded by the inspection apparatus and is also communicatively coupled to a training system 130. The computer system 120 uses the data received from the inspection apparatus 110 and correlation information received from the training system 130 as inputs to a defect identification and quantification module (IDQ) 122, which generates a defect quantification report providing the type, size, depth, orientation and entrapped media information for any defect identified on the structure surface. The computer system 120 can be implemented onsite using any computing device having sufficient processing and memory resources (e.g., a single or multicore processor and solid-state memory), including a laptop, tablet or any other computing device readily accessible during an onsite inspection.

The training system 130 includes at least one processor that is operative to execute several modules. As will be described in greater detail below, the modules include a defect microstructure database (DMDB) module 132 that comprises code that causes the at least one processor to use relevant inputs to generate a set of modeled structural defects, each defect of the database having a specific type, size, depth, orientation and entrapped media. The defects are stored in an associated DMDB database. The training system 130 also includes a virtual thermograph database (VTDB) module 134 that comprises code that causes the at least one processor to run mathematical simulations which calculate expected responses of the microstructure defects within the DMDB database 132 to heating, and which causes the at least one processor to generate virtual thermographs of the expected infrared radiation emissions from each of the microstructures. The virtual thermographs are stored in a VTDB database. The training system 130 also includes an expert system module 136 that executes a machine learning algorithm as may be implemented in the processor (e.g., as computer code), such as a neural network, to correlate the virtual thermographs output by the VTDB module 134 with the parameters of the defects in the DMDB database 132. An optimized acquisition parameter (OAP) module 138 comprises code that causes the at least one processor to automatically determine optimal parameters for controlling the inspection apparatus 110 including optimal heating parameters such as heating mode, heating time, acquisition time, heat flux, etc. based on inputs including the properties of the inspected composite material and environmental and operating conditions. Modules 132, 134, 136, 138 can include and/or make use of processing resources for executing computer program instructions which generate data, and also employ memory resources for storing the generated data. All of the processes executed by training system 130 can be executed before an inspection of an actual structure.

The computing resources allocated for the training system 130 can be co-located on a single computing system or at a single facility or, alternatively, can be distributed across multiple computing systems and at a single or multiple facilities. Additionally, the training system can be hosted on fixed systems or can be hosted on the cloud on a virtual computing platform. In certain embodiments, distributed computing resources implement code that cause one or more of the computing resources to pause or cease one or more operations as a function of the operational state or particular data of another one of the computing resources. In such an embodiment, computational resources are preserved by controlling operations in response to coordinated communications among such resources in view of operational state updates or particular data.

Inspection Apparatus

Figure 2A:
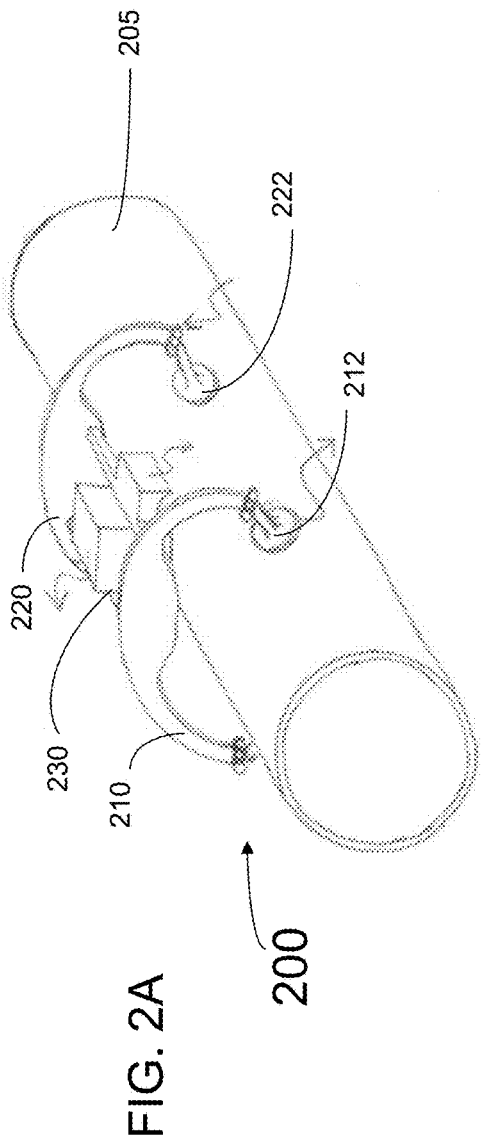
FIG. 2A is a perspective view of an exemplary embodiment of an inspection apparatus according to the present invention.

FIG. 2A is a perspective view of an embodiment of an inspection apparatus 200 according to the principles disclosed herein. The apparatus 200 is shown affixed to a pipe structure 205 made of a composite that is to be inspected. Apparatus 200 includes adjustable supporting clamps 210, 220 that are used to firmly and removably position and affix the apparatus 200 at a desired position on the structure 205 to inspect a particular surface section. Clamps 210, 220 are curved to adapt to structures having different circumferences. The ends of clamps 210, 220 terminate at respective suction pads e.g., 212, 222 (pads on the reverse side of the structure 205 are not shown) or other suitable mechanism for firmly and removably affixing the clamp ends to the surface of the structure 205. A semi-enclosed chassis unit 230 is coupled to and positioned between the clamps 210, 220. In the embodiment depicted the chassis unit 230 includes the components used for inspection as will be described further below. The chassis unit 230 can be fixedly attached to the clamps 210, 220 by bar elements as shown, or alternatively, chassis unit 230 can be removably coupled to the clamps in other implementations.

Figure 2B:
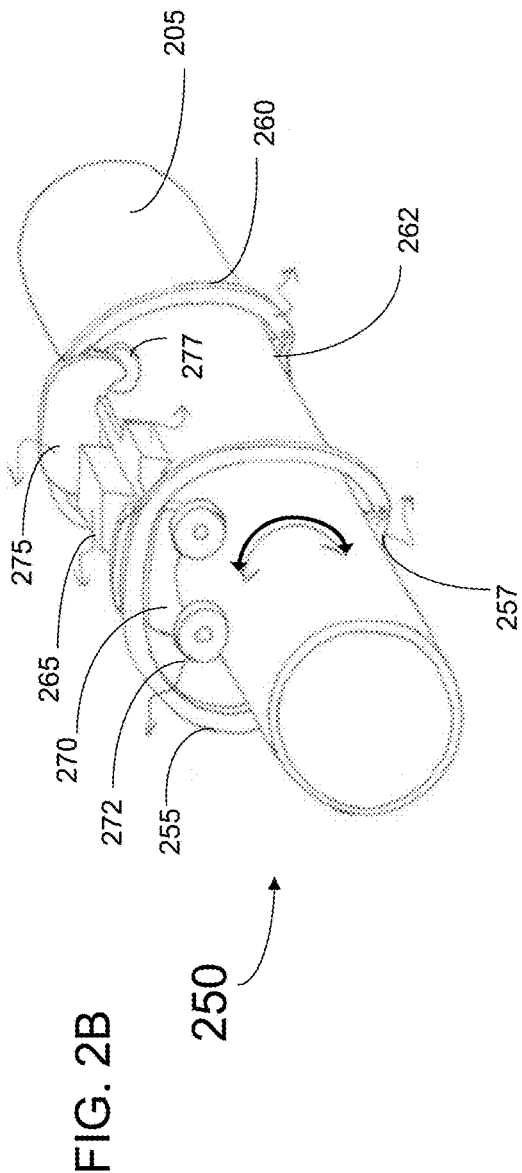
FIG. 2B is a perspective view of another exemplary embodiment of an inspection apparatus according to the present invention that can move circumferentially around an inspected structure.

FIG. 2B is a perspective view of another embodiment of an inspection apparatus 250 according to the principles disclosed herein. In this embodiment, clamps are replaced with slide guides 255, 260 that extend further around structure 205 and similarly end in respective suction pads, e.g., 257, 262. A chassis unit 265 including the components used for inspection is coupled on first and second sides to sliding elements 270, 275. In the embodiment depicted, the sliding elements 270, 275 are implemented as semicircular-shaped components, each having a groove with which they mate to respective slide guides 255, 260. Sliding elements 270, 275 include respective sets of wheels 272, 277 with which they movably grip the surface of substrate 205. As depicted, the chassis unit 265 is coupled to sliding elements which are movable circumferentially around the structure as constrained by the slide guides 255, 260. This allows the chassis unit 265 to be carried circumferentially by movement of the sliding elements 270, 275. Wheels 272, 277 can be moved either manually or remotely (electronically) to actuate the sliding motion, and the inspection apparatus 250 can be moved automatically around the circumference to inspect a number of sections on the surface of the substrate sequentially. This enables the operator to scan large areas of the structure 205 while employing a single configuration and setup of the inspection apparatus 250.

Figure 2C:
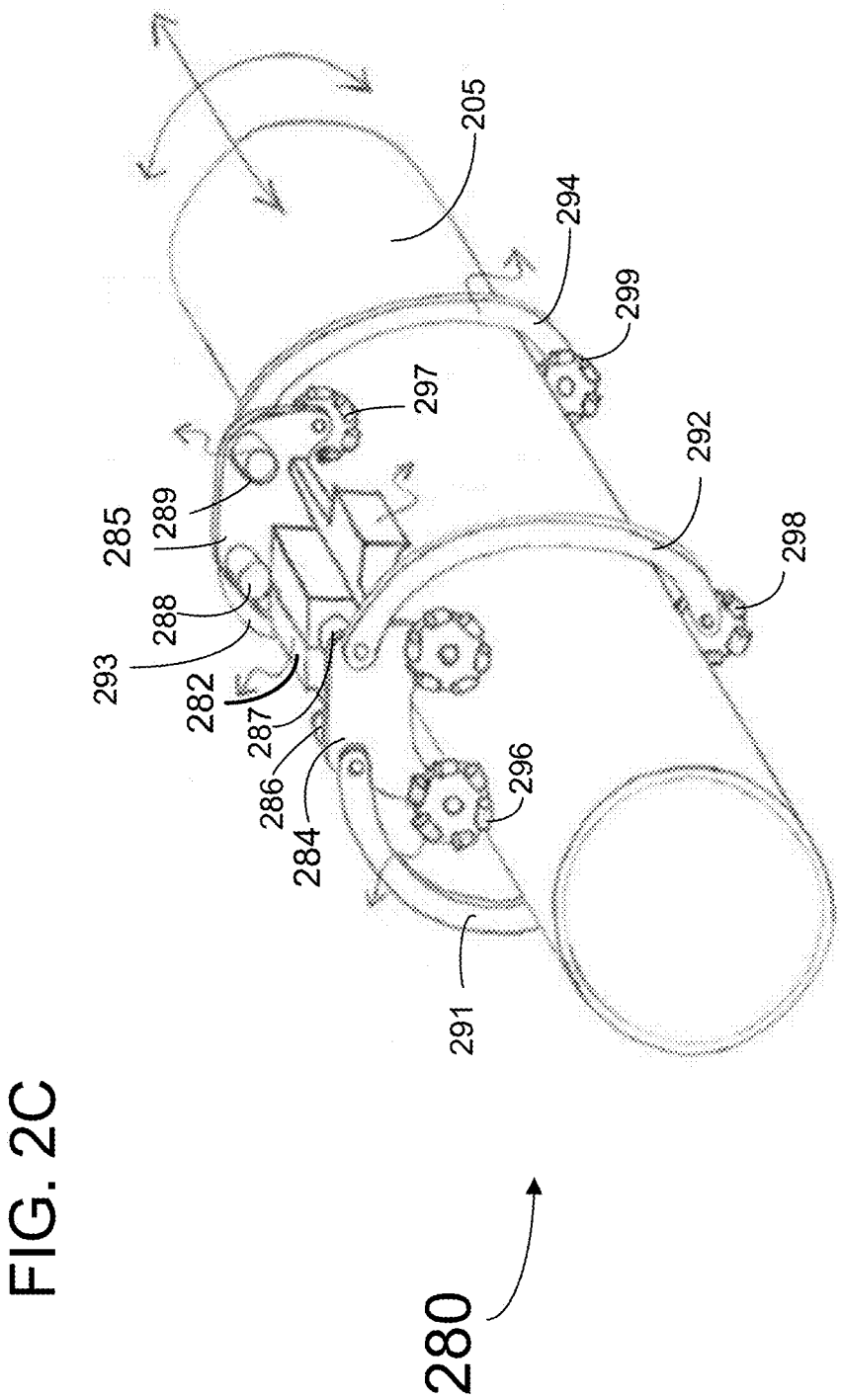
FIG. 2C is a perspective view of another exemplary embodiment of an inspection apparatus according to the present invention that can move both circumferentially and longitudinally along an inspected structure.

FIG. 2C is a perspective view of a further embodiment of an inspection apparatus 280 according to the present invention that provides both circumferential (rotational) and longitudinal movement (translation) of the apparatus 280 along a structure 205. Chassis 282 is coupled on either side to sliding elements 284, 285. Spring elements 286, 287 are attached to sliding element 284 and springs elements 288, 289 are attached to the sliding element 285. Spring elements 286-289 can be implemented using torsion springs. Springs 286-289 aid in fixing the chassis 282 at a specific position on structure 205 during an inspection. Latching arms 291, 292 are pivotably coupled to sliding element 284, and latching arms 293, 294 are pivotably coupled to sliding element 285. Wheels, e.g. 296, 297 are coupled to the bottom of respective sliding elements 284, 285 and wheels, e.g., 298, 299 are coupled to the distal ends of latching arms 291, 292, 293, 294. The wheels, e.g., 296-299 are preferably implemented using Omniwheels that can both slide and rotate on their axes enabling the apparatus 280 to be moved either manually or remotely (electronically) in both circumferential and longitudinal directions with respect to structure 205. This embodiment also enables the operator to scan large areas of the structure 205 while employing a single configuration and setup of the inspection apparatus 250.

FIG. 3 is a schematic diagram showing an embodiment of the components of a chassis unit 300 that can be implemented in the apparatuses 200, 250, 280 to perform the inspection of the composite structure by active infrared thermography. Active thermography involves heating the surface of an inspected area to create a difference between the temperature of the surface immediately above the defect and the surrounding temperature. The heating produces an internal heat flux within a certain depth of the surface. Subsurface defects affect the heat diffusion and produce corresponding thermal contrasts which are reflected in the infrared radiation emitted from the surface. Defects, which block and slow diffusion of heat within the material, are detected by the manner in which the captured infrared radiation changes over time. Typically, sub-surface defects cause the surface immediately above the defect to cool at a different rate than the surrounding areas.

Turning to FIG. 3, the chassis unit 300 is semi-enclosed and the side of the unit that faces the structure surface is open at least in part to permit a heating device 310 and an infrared camera 320 to extend outwardly from the enclosure of the housing toward the surface. The heating device 310 is operable to emit radiation toward a section of the surface during an inspection. An infrared camera 320 is operable to detect infrared radiation emitted back from the surface in response to heating. Both the heating device 310 and the infrared camera 320 operate at a distance from the surface of the structure. FIG. 4A is a schematic illustration of one implementation of the heating device 310 and infrared camera 320. In this figure the heating device 310 comprises two heating lamps 405, 410 arranged adjacent to one another so as to emit a cone of radiation 412 to cover an area of surface of a structure 415. The radiation causes a heat flux 420 beneath the surface of structure 415, and infrared camera 320 is positioned centrally to receive an optimal intensity of infrared radiation 425 emitted from the surface. An exemplary defect 430 is shown located at a depth beneath surface 415. The heating device 310 can also include a hood 435 as a protection against the intense radiation emitted by the heating device 310. The infrared camera 320 is adjustable to optimize acquisition of emitted infrared radiation and can be positioned centrally between the heating lamps 405, 410 (as shown in FIG. 4A) or adjacent to the heating elements as shown in FIG. 3, and oriented at various angles with respect to the surface of the inspected structure.

Referring again to FIG. 3, chassis unit 300 also includes a controller 330 (e.g., a microcontroller or processor) operative to control the heating device 310 and infrared camera 320. Controller 330 is also coupled to a memory unit 340 and to a transceiver 350 with which it is communicatively coupled to computer system 120 (of FIG. 1). Transceiver 350 can conduct communication using various communication modes including Wi-Fi, RF and Zigbee protocols to achieve two-way data transmission between the inspection apparatus and online computer system 120.

Heating lamps used for infrared thermography typically employ xenon flashtubes. During operation, lamps 405, 410 produce flashes of light in response to trigger signals from controller 330. After activating the lamps 405, 410, the controller 330 activates the infrared camera 320 to periodically capture successive digital images of the radiative emissions of the heated portion of the inspected surface. The infrared camera 320 can be coupled to a motor operated by controller 330 to change the angle and distance between the camera and the inspected surface to achieve a suitable focus on the surface. The digital image data generated by the infrared camera 320 can be transferred to and stored in memory unit 340. The controller 330 utilizes transceiver 350 to transfer the digital image data from the memory unit 340 to computer system 120. The controller 330 can also perform some pre-processing of the digital image data prior to transmission to computer system 120. For example, as the inspection apparatus is moved and images are captured from adjacent surface sections, the controller 330 can format the data into discrete image frames. Alternatively, such preliminary image processing can be performed at computer system 120.

Among several active infrared known infrared thermography excitation methods, pulsed thermography and lock-in thermography have been widely used. FIG. 4B is a graph of the amplitude (intensity) of activation radiation provided over time (above), and amplitude of infrared radiation emitted from the surface over time (below). As indicated, in pulse thermography a pulse of high energy over short-duration is applied to a surface and the amplitude of infrared radiation emitted back from the surface rises sharply in response, and then starts to fall as soon as the activation pulse ends. Presence of a defect is indicated by the relatively slower rate at which the amplitude of infrared radiation emitted from the surface declines (i.e., the slower rate at which the surface cools). FIG. 4C is a similar graph of amplitude versus time showing a continuous, e.g., sinusoidal activation and a corresponding sinusoidal infrared response. As indicated, in lock-in thermography, presence of a defect is not shown in a different in amplitude response, but rather in a phase shift between the input activation energy and the surface temperature response. The phase analysis of lock-in thermography has the advantage of being less sensitive to the local variations of illumination or surface emissivity in comparison to pulsed thermography. However, either or both of pulsed and lock-in thermography as well as other excitation methods can be used.

As inspection of the composite structure is performed, with periodic heat activation and acquisition of infrared image data, the controller 330 preferably receives and transfers the digital image data in real time wirelessly as a video stream to computer system 120 for analysis and identification of defects.

Themography Training Method

Figure 5:
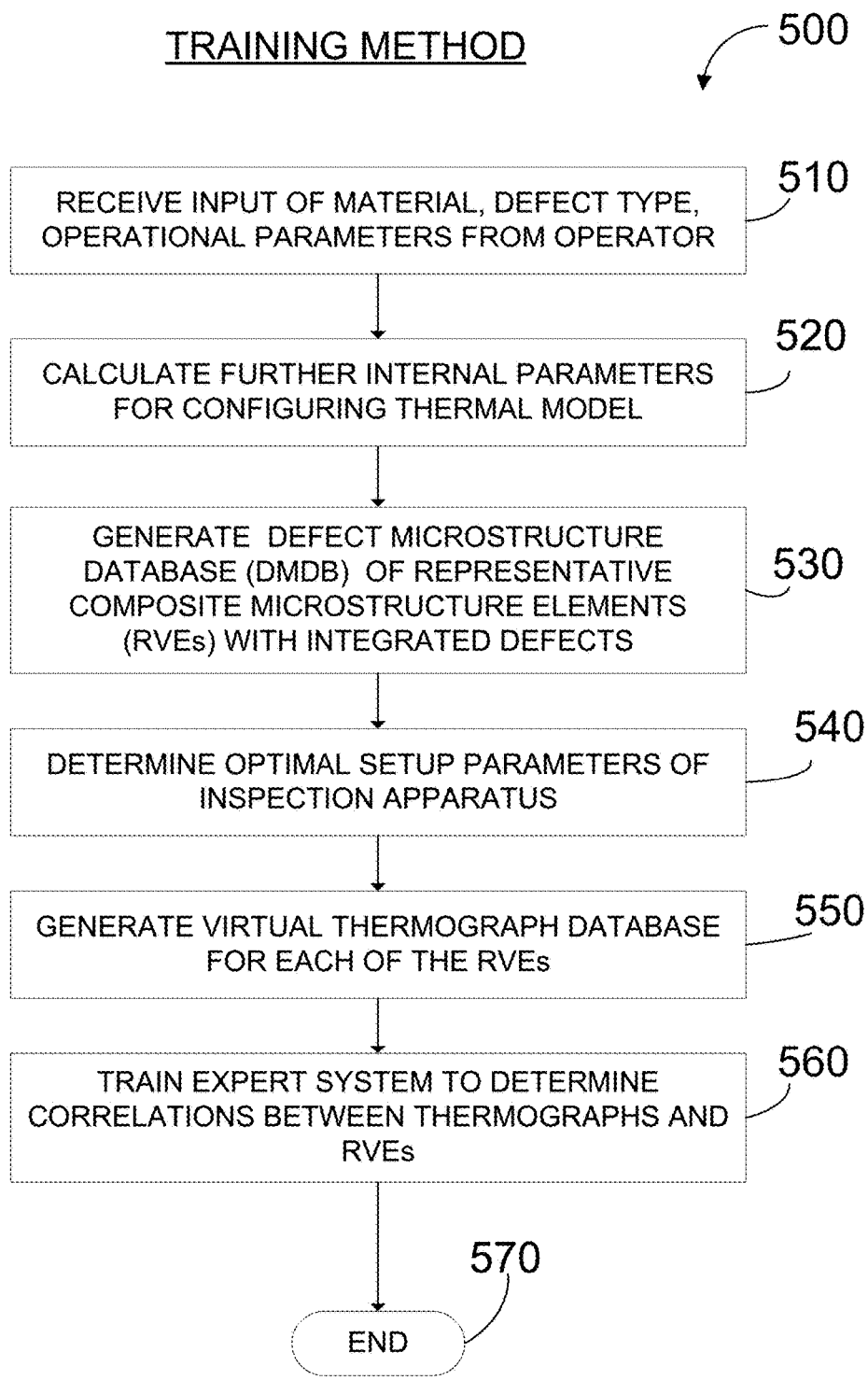
FIG. 5 is a flow chart of a method of training an expert system to correlate virtual thermographs with characteristics of modeled defects (RVEs) according to an exemplary embodiment of the present invention.

Before turning to the analysis of the data acquired by the inspection apparatus, we turn first to a description of the inventive training method which enables the analysis to achieve accurate quantitative data concerning defects in a structure. FIG. 5 is a schematic flow chart of an embodiment of the training method 500 as disclosed herein. The training method includes several distinct procedures: i) input of relevant data by an operator via a user interface (510); ii) automatic configuration of internal parameters (520); iii) generation of a database of representative microstructures (DMDB) with integrated defects (530); iv) determination of optimal setup parameters of the inspection apparatus for data acquisition (540); v) generation of a virtual thermograph database (VTDB) by simulation (550); and vi) training of an expert system to determine correlations between the microstructures of the DMDB and the thermographs of the VTDB generated by simulation (560). Each of procedures (i) to (vi) are described in turn. It is noted, however, that in alternative embodiments, a subset of these procedures can be performed without departing from the principles disclosed herein.

Figure 6:
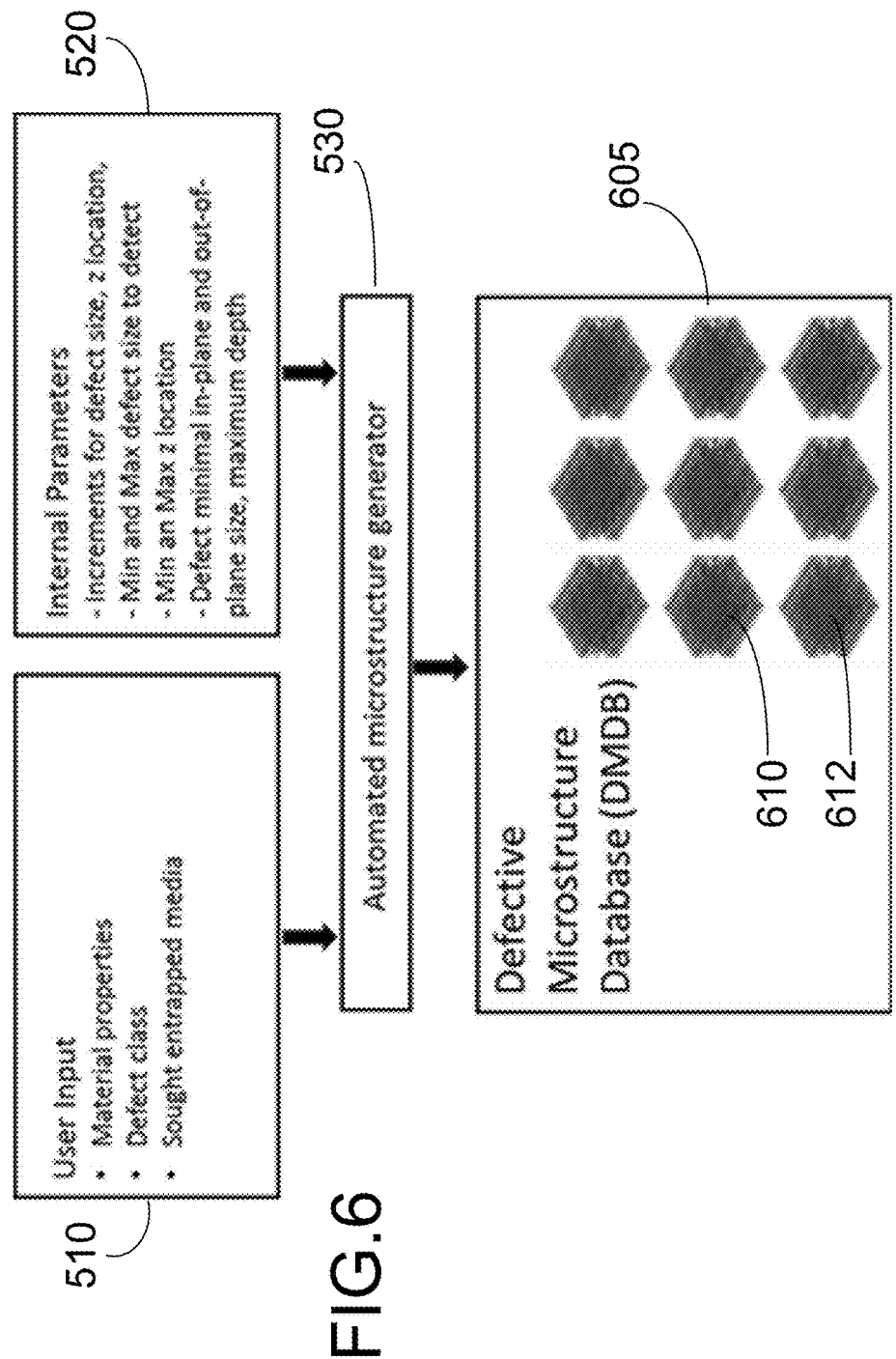
FIG. 6 is schematic flow chart of a method of generating a defective microstructure database (DVDB) according to an exemplary embodiment of the present invention.

FIG. 6 is a schematic view of an embodiment of the first three procedures 510, 520, 530 of the training method outlined above. As depicted in step 510, inputs including material, structural and environmental properties are entered into the training system 130 by an operator in order to model and store a set of representative microstructures containing specific defects. The possible material properties include parameters, such as, but not limited to: resin and fiber thermal conductivity, specific heat, fiber volume content, fraction of porosity, ply thickness, layup sequence, fiber orientation per ply, internal and/or external coating thickness. Input structural properties include the diameter and thickness of the material. Environmental and operating properties include parameters, such as, but not limited to: operating pressure, transported fluid temperature and flow velocity, ambient temperature, and high temperature points in proximity to the inspected structure. In addition, the operator inputs set the defect type and entrapped media for each microstructure. The possible defect types include, among others: delamination, unique void, matrix cracking, fiber-matrix de-bonding, multiple voids, and holes. Entrapped media constitutes fluid or gas entrapped within the defects, which are typically air, water or oil. The parameters set forth are exemplary and do not constitute an exhaustive listing of all parameters or types that can be entered into the training system by operators.

In addition to the parameters entered by operators of the training system, the training system generates internal parameters in step 520. The internal parameters are used to initialize and configure a thermal simulation model and can include, among other internal parameters, a selection from among: heat flux over the material surface over time, increments for defect size, depth location, minimum and maximum defect size, minimum and maximum out-of-plane size, minimum and maximum depth, mesh discretization, and other thresholds for setting bounds on the parameters of defects. The internal parameters can be modifiable by the operator.

Figure 7A:
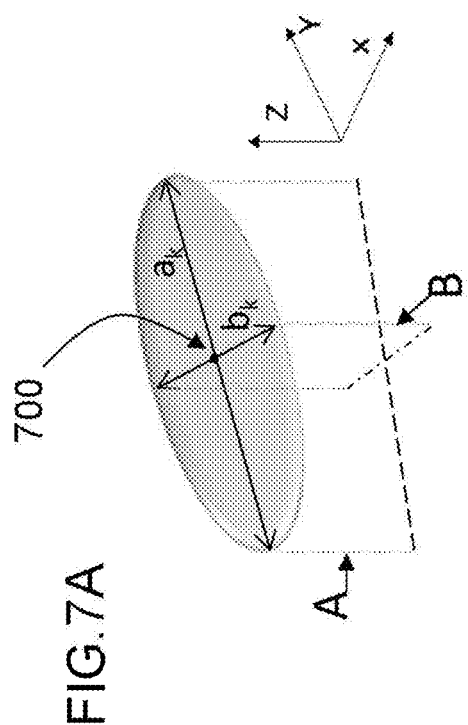
FIG. 7A is a schematic perspective illustration of a representative volume element (RVE) according to an exemplary embodiment of the present invention.
Figure 7B:
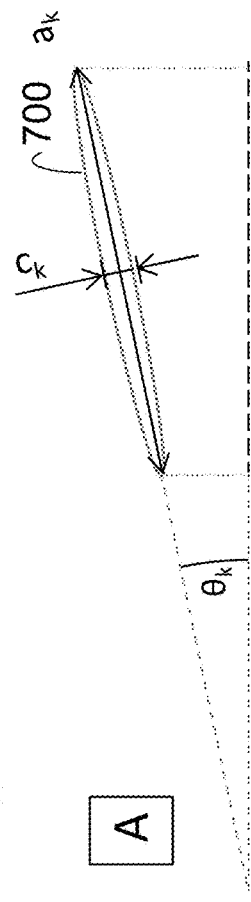
FIG. 7B is cross-sectional view of the RVE of FIG. 7A taken along axis A.
Figure 7C:
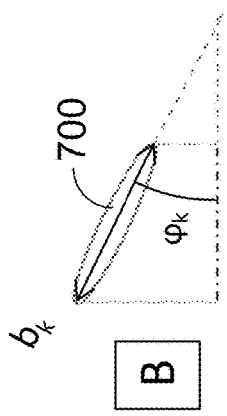
FIG. 7C is a cross-sectional of the RVE of FIG. 7A taken along axis B.

The defect microstructure database (DMDB) module 132 uses the operator input and internally generates parameters, in step 530, to generate a database (DMDB) 605 that includes a number (N) of models of small structural elements, referred to herein as microstructures, e.g. 610, 612, with each microstructure having specific parameters and at least one integrated defect. The number (N) can also be controlled by the operator through control over increment sizes. In some implementations, N is in a range of 1,000 to 50,000. However, a greater or smaller number of microstructures can be generated. Each entry of the database, termed a "representative volume element" (RVE) can be parameterized as a vector of eight elements $V_k$ [ $a_k$, $b_k$, $c_k$, $z_k$, $\theta_k$, $\varphi_k$, $M_k$] where $z_k$ is the coordinate of the defect centroid in the out-of-plane direction (perpendicular to the inspection plane) in the kth RVE, $a_k$, $b_k$ and $c_k$ are the spatial dimensions of the defect within the kth RVE, $\theta_k$ and $\varphi_k$ are the angles between the plane of the defect and the inspection plane, $D_k$ is the defect type, and $M_k$ is the type of media entrapped within the defect. FIG. 7A is a schematic representation of an example RVE defect stored in the defect microstructure database (DMDB). The defect 700 is modeled as an ellipsoid in which $z_k$ defines the location of the center of the defect across the composite thickness, $a_k$, $b_k$, $c_k$ define the length, width and thickness of the defect and angles $\theta_k$ and $\phi_k$ in cross-sectional planes A and B define the position and orientation of the defect with respect to the surface of the composite structure (the inspection plane). In the example depicted in FIG. 7A, the defect is an isolated delamination which is indicated by parameter $D_k$, and the entrapped media is air, indicated by parameter $M_k$. While the model simplifies the geometry of defects to some extent, the large number and variation in location, sizes, defect types and entrapped media generated in practice cover and suitably represent typical defects that occur in composite structures. FIG. 7B is a cross-sectional view of RVE 700 taken along axis A showing first orientation angle $\theta_k$ of the RVE with respect to the inspection plane. FIG. 7C is an analogous cross-section view of RVE 700 taken along axis B showing a second orientation angle $\phi k$ of the RVE with respect to the inspection plane.

Figure 8:
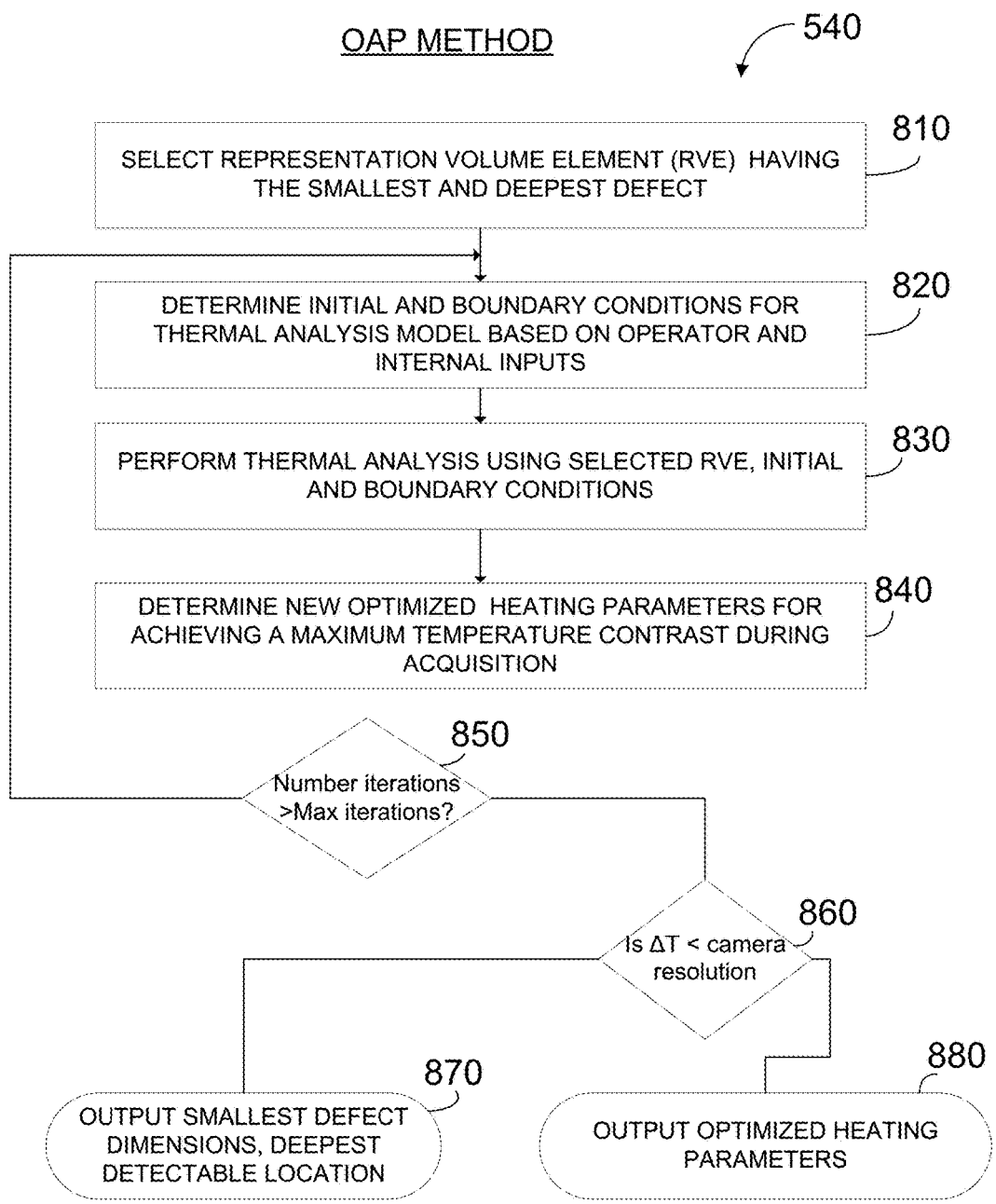
FIG. 8 is a flow chart of a method of automatically generating optimized acquisition parameters according to an exemplary embodiment of the present invention.

In step 540 of the training method 500, the optimized acquisition parameter (OAP) module 138 uses the operator input including material properties and operating conditions as well as internally generated parameters to determine optimal infrared thermography parameters for configuring an inspection apparatus. FIG. 8 is a flow chart of the OAP determination method 540. In a first step 810, the DMDB is searched and the RVE that has the smallest and/or deepest defect is selected. In step 820, the OAP module 138 determines initial and boundary conditions for a thermal simulation model of the selected RVE using the initial parameters, which here are the parameters for heating flux ($\Delta H_f$), heating period ($\Delta H_p$), heating mode (e.g., continuous, modulated, pulsed) and camera acquisition time ($\Delta t$) generated in step 520 of the training method. However, it is noted that the heating parameters will depend on the heating mode (e.g., flash, pulse, continuous). For example, in pulse mode, the frequency of the heating pulse will be a controlled parameter.

In step 830, an analysis of thermal response of the least thermally responsive RVE of the DMDB (smallest and deepest defect) is performed. In some implementations, the thermal simulation employs finite element analysis. As will be understood by those of skill in the art, finite element analysis is a way to find approximate solution to boundary value problems for physical systems that involve partial differential equations. Heat flow is characterized by partial differential equations of this type and finite element analysis is often employed in providing solutions in this field. Finite element analysis includes the use of mesh generation techniques for dividing a complex problem into small elements, as well as the use of a finite element simulation that determines solutions to sets of equations for each of the finite elements as well as a global solution to the entire domain. Following completion of the thermal simulation of the selected least thermally responsive RVE, in step 840, the OAP module 138 determines, based on the input parameters and thermal analysis, new optimized heating parameters such as, but not limited to $\Delta H_f$, $\Delta H_p$, $\Delta t$ parameters, in the example being discussed, in order to achieve a maximum temperature contrast during data acquisition.

The optimization of the heating parameters is iterative and the method performs a certain number of iterations before outputting optimized values. Accordingly, in step 850 it is determined whether the number of iterations performed thus far has reached a selectable threshold (MaxIterations). If MaxIterations has not been reached, the process flows back from step 840 to step 820. Alternatively, if MaxIterations has been reached, in step 860 it is determined whether the value for the determined maximum temperature contrast ($\Delta T$) remains lower than the infrared camera sensitivity. If $\Delta T$ is lower than the camera sensitivity, in step 870, the OAP module 138 outputs: 1) the smallest diameter expected to be detectable for a given depth; 2) the smallest expected thickness detectable for a given depth; and 3) the greatest expected depth detectable within the breadth of a defect for a given defect diameter. If $\Delta T$ is above the threshold, in step 880 the OAP module outputs the current optimized values for heating parameters (e.g., heating mode, $\Delta H_f$, $\Delta H_p$, $\Delta t$) from the last iteration of the method.

Figure 9:
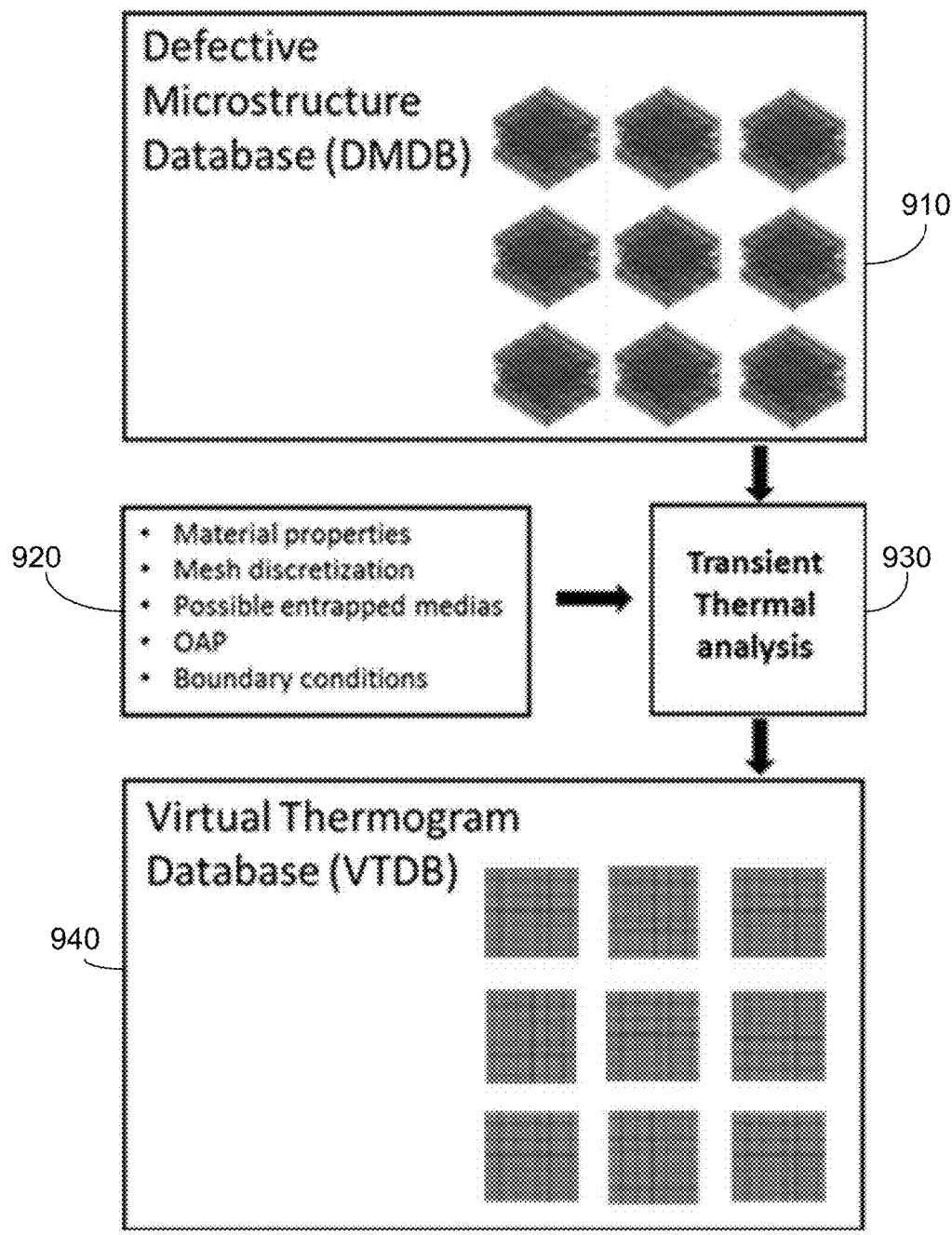
FIG. 9 is a schematic flow chart of a method of generating a virtual thermograph database (VTDB) according to an exemplary embodiment of the present invention.
Figure 10A:
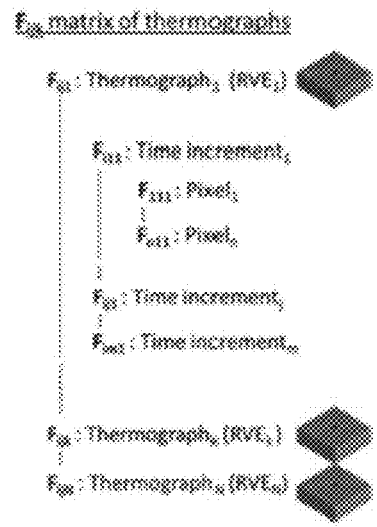
FIG. 10A is a schematic illustration of an exemplary matrix data structure for storing thermograph data generated by according to embodiments of the present invention.
Figure 10B:
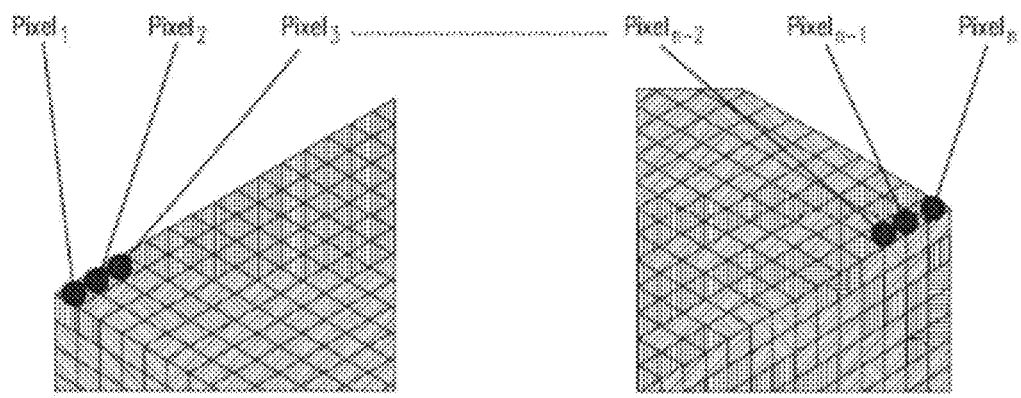
FIG. 10B is a schematic graphical illustration of an embodiment of the matrix data structure of FIG. 10A for a specific RVE.

Returning to FIG. 5, the accumulated data entered or generated in steps 510, 520, 530 and 540 are used as inputs in step 550, in which virtual thermograph module 134 executes a transient thermal analysis (TTA) simulation that outputs 'virtual' thermographs for each element (N) in the DMDB. More specifically, as schematically illustrated in FIG. 9, the TTA simulator receives as inputs all of the elements in the defective microstructure database 910 and the combined operator input, internally-generated parameters, boundary conditions and output of the OAP module ("combined inputs"). The TTA simulation is a parametric, mathematical model that can be implemented using finite element analysis. In such a finite element analysis, N separate analyses are carried out corresponding to the N RVEs contained in the DMDB 910. The output of each finite element analysis is a transient 'virtual' thermograph of the outer surface of a structural element, i.e., a set of graphs showing thermal response of the surface over time. Generally, the expected accuracy of the finite analysis depends on the number of elements in the DMDB 910 (i.e., the value of N), with higher values of N improving the expected accuracy The thermograph data is output and formatted as a matrix $F_{ijk}$ in a visual thermograph database (VTDB) 940, where i represents the ith camera pixel element, j represents the jth time increment, and k represents the kth RVE. FIG. 10A provides an illustration of the data structure of matrix $F_{ijk}$. In the figure $F_{ij1}$ represents all of the elements of matrix pertaining to the first RVE (k=1). Nested within $F_{ij1}$ are entries $F_{i11}$ within which, in turn, are nested elements $F_{111}$ through $F_{n11}$. Elements $F_{111}$ through $F_{n11}$ represent all of the recorded pixels during the first time increment for the first RVE (j=1, k=1). Accordingly, for each of the N RVEs there are associated m time increments, and during each time increment, n pixel values are generated. FIG. 10B is a schematic perspective illustration of a thermograph at a given time increment, indicating how the thermographs for a given RVE can be envisioned as a block of m thermographs, with each thermograph having n pixels. As can be discerned, a high resolution simulation can generate a large amount of data. However, as the training system 130 performs analysis offline, there is no fixed limit to the resources that can be allocated to the transient thermal analysis. Moreover, the resolution level can be varied by the operator if resources or efficiency are limiting factor in a particular scenario.

With a database of thermographs of sufficient precision and accuracy, it is possible to compare thermographs of a composite structure acquired during inspection runs in the field with thermographs in the database to identify any defects present in the structure. However, it is computationally expensive to compare entire images for matching, and even more so to compare the evolution of images (transient response) over time. One way to solve this problem is by training the system to correlate the virtual thermographs with the parameters of the RVEs from which they are derived. In this way, when thermographs are acquired in the field, they can be analyzed without having to search through an image database.

Figure 11:
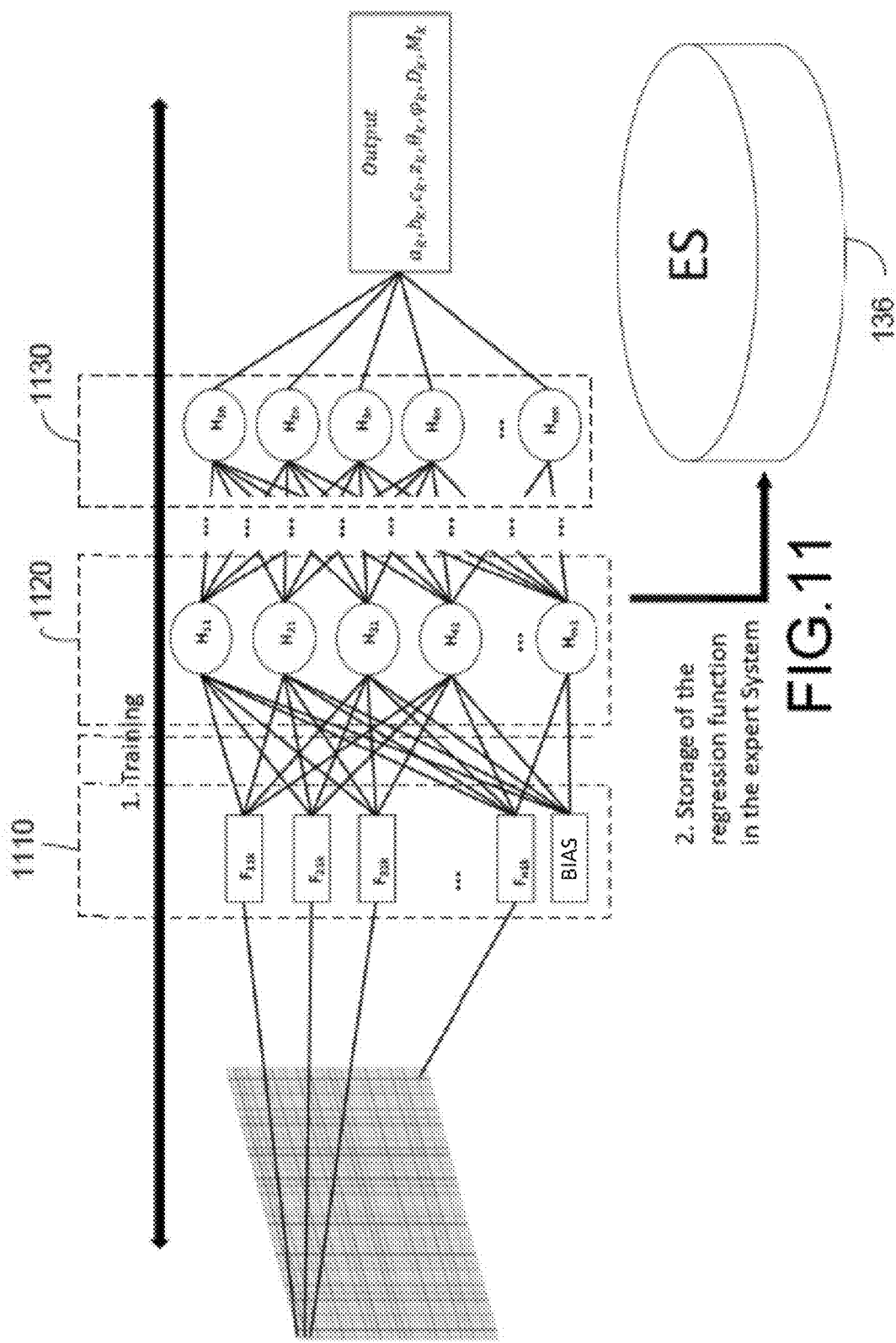
FIG. 11 is a schematic diagram of an exemplary neural network that can be employed in the expert system training method according to embodiments of the present invention.

Therefore, in step 560 of the training method, an expert system is trained by a machine learning process to correlate the images of the virtual thermograph database with the parameters of the RVEs from which they are derived. In some implementations, the expert system module 136 of training system 130 employs a neural network algorithm, shown in FIG. 11, as the machine learning technique. Neural network 1100 includes an input layer 1110, one or more hidden layers 1120 and an output layer 1130. The input layer 1110 includes all of the pixels of a virtual thermograph of the VTDB for a given RVE at a particular time increment, and the output layer 1130 includes the parameters of the same RVE including its position, orientation, defect dimensions, defect type and entrapped media. The neural network correlates the input layer 1110 to the output layer 1130 by use of one or more hidden layers 1120. Each of the inputs in the input layer 1110 is multiplied by coefficient factors in the hidden layer(s) 1120 to yield the output layer 1130. The coefficients of the hidden layers 1120 are determined by a process of backward propagation in which a cost function is minimized. This yields an optimized correlation between the virtual thermographs and the RVE parameters. The expert system module 136 stores the coefficients for further use. After the expert system training is complete, the training method ends in step 570.

Real-Time Inspection Method

Figure 12:
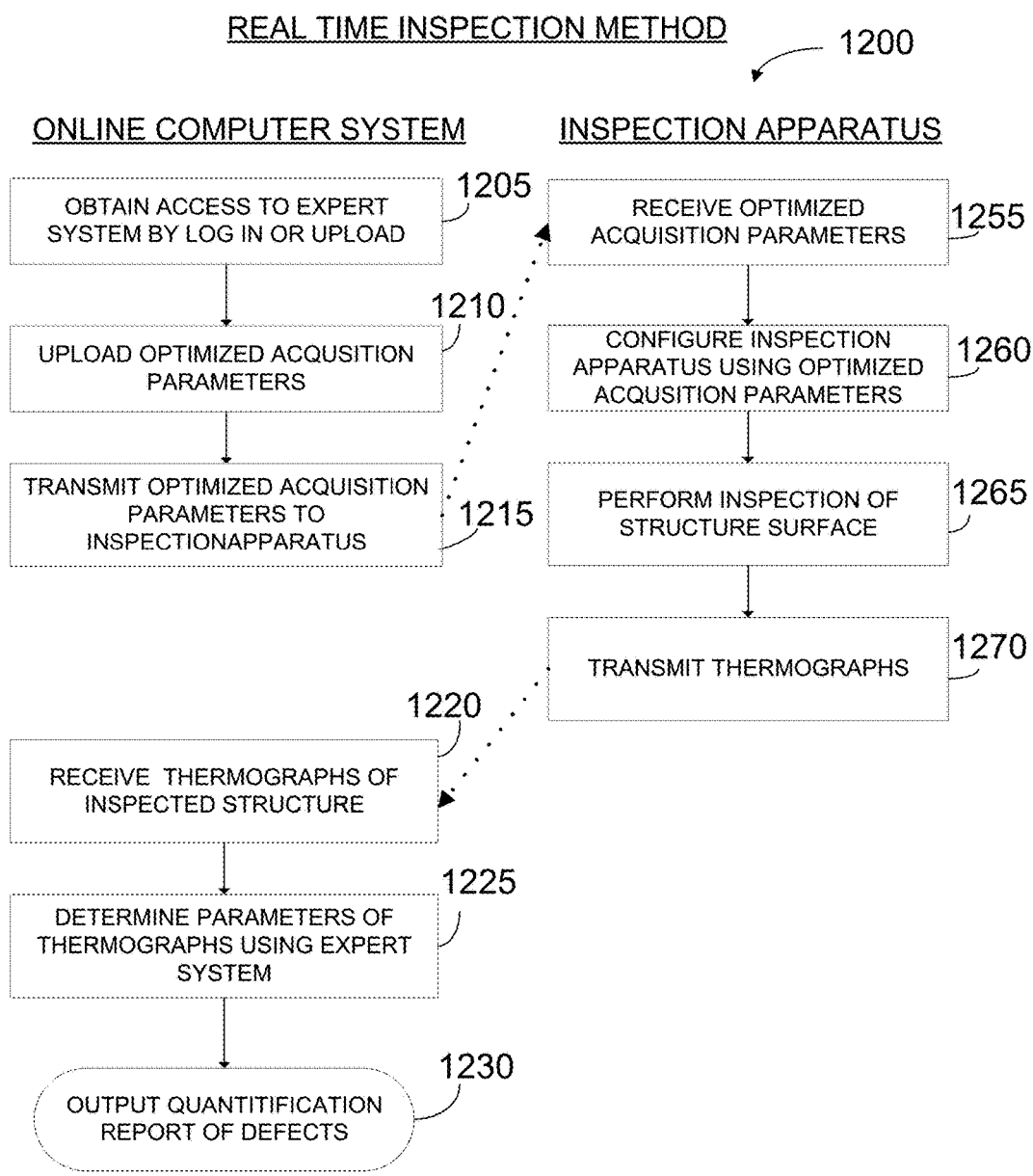
FIG. 12 is a flow chart of a method for real time inspection of a structure according to an exemplary embodiment of the present invention.

Flow charts of the sub-parts of a real time inspection method 1200 performed by the online computer system 120 and inspection apparatus 110, respectively, are shown in FIG. 12. As noted above, the expert system is generated and stored off-site at a remotely located facility. In order for operators at a field site to perform a structural inspection to be able to utilize the expert system, access to the expert system at the onsite location is required. In a first step 1205, an operator obtains access to the expert system either by logging into an expert system server over a network using online computer system or alternatively, by directly downloading the expert system algorithm and stored data from the training system 130 onto the online computer system 120. Additionally, the expert system can be downloaded by a using a storage medium such as a flash drive. In step 1210, the online computer system uploads optimized acquisition parameters from the OAP module 138 of training system 130. In a following step 1215, the online computer system 120 transmits the optimized acquisition parameters to the transceiver 350 of inspection apparatus 110.

In step 1255, inspection apparatus 110 receives the optimized acquisition parameters from online computer system 120. Using the acquired parameters, in step 1260, the controller 330 of inspection apparatus 110 configures heating and acquisition parameters for operating the heating device 310 and infrared camera 320. Upon configuration, the inspection apparatus is configured to apply radiation and capture infrared radiation for the smallest and deepest defect that is within the detection capability of the infrared camera, so that the inspection apparatus as a whole has maximum sensitivity for the given hardware capabilities. In step 1265, the inspection apparatus performs an inspection in which a section of an inspected surface is heated by heating device 310 and infrared radiation acquired by infrared camera 320. During inspection, the inspection apparatus can be fixed in position to inspect a specific area of a structure, or the inspection apparatus can be controlled to move in a particular trajectory to inspect different areas or the entire surface of a structure. In real time or approximate real time, in step 1270, the controller compiles the infrared radiation data acquired by the infrared camera and transmits the data in the form of thermographs to computer system 120 via transceiver 350.

Figure 13:
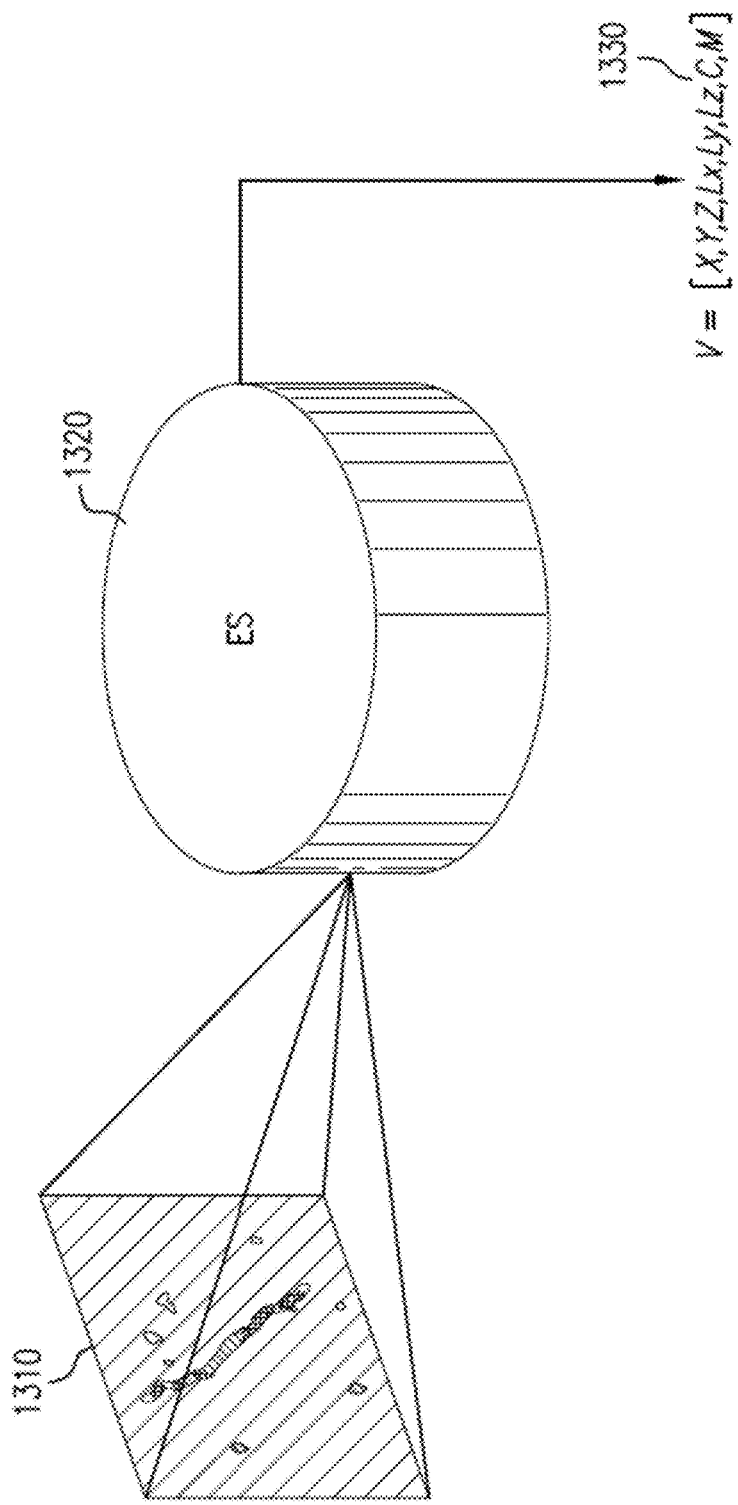
FIG. 13 is a schematic diagram of a process of analyzing an acquired thermograph using an expert system to yield defect parameters according to an exemplary embodiment of the present invention.
Figure 14:
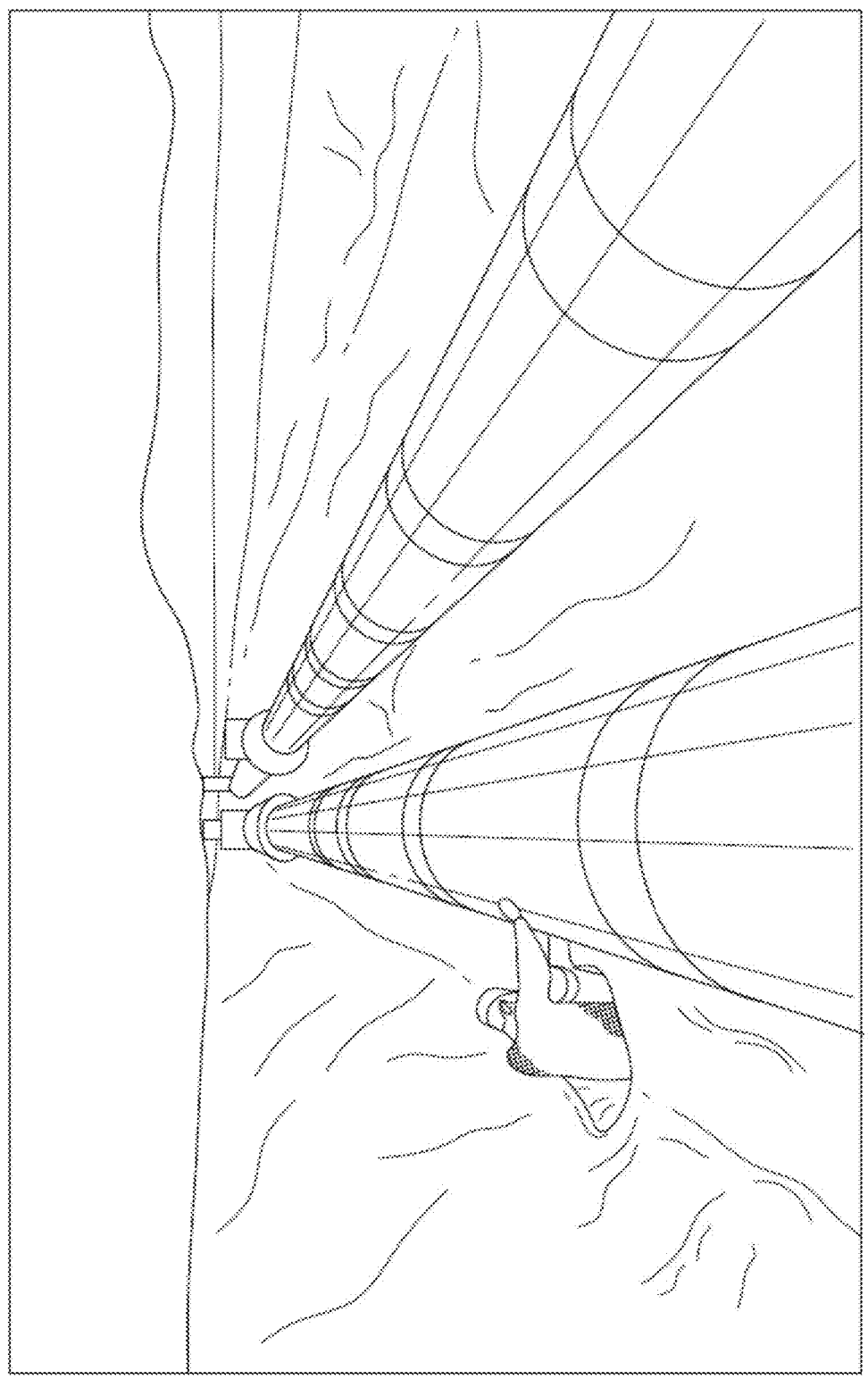
FIG. 14 is a photograph of a large pipeline made of composite material.

Computer system 120 receives the thermographs in step 1220, and in step 1225, performs real-time quantification of defects in the inspected structure based on the acquired thermographs. Step 1225 is schematically illustrated in FIG. 13 which illustrates a thermograph 1310 input to expert system 1320. Expert system 1320 in this case is the module executed on computer system 120 (as opposed to the training system 130) and, as noted above, can represent a client of an expert system server, or a software module executed on computer system 120 that emulates aspects of the expert system module 136 of the training system 130. In some implementations, expert system 1320 can be a copy of the expert system module 136 uploaded from the training system 130. Expert system 1320 applies the correlations obtained from the training system 130 to the acquired thermograph and outputs a defect parameter vector including the elements described above with reference to FIG. 7. The defect parameter vector identifies the defect in terms of its type, size, depth, orientation and entrapped media. The online computer system then, in step 1230, generates a defect quantification report that includes the thermographs acquired in real time and the characteristics of any detected defects.

The disclosed apparatus, system and methods for inspecting structures using quantitative infrared thermography provide several advantageous features. The system and methods are easy to implement as, in some embodiments, the inspection apparatus can move automatically around and along the inspected structure, reducing manual inspection procedures. In addition, embodiments of the inspection apparatus are designed to progress rapidly over inspected structures, further reducing interventions in the inspection process. The disclosed system also delivers inspection results in real-time, allowing the possibility of initiating remedial measures onsite to remove serious defects. The inspection apparatus is contact free and relatively cost effective; the infrared camera is the highest expense in most implementations. Moreover, the system provides unbiased configuration of the inspection apparatus since optimization parameters for data acquisition are determined by the system independently from the operator. Likewise, inspection results are unbiased as they are generated independently from human expert knowledge or expertise. The large number of virtual samples While the apparatus, system and methods disclosed herein are particularly intended to be used for composite inspection and defect detection, with suitable modifications, the inventive techniques can be applied to other materials.

It is to be understood that any structural and functional details disclosed herein are not to be interpreted as limiting the apparatus, system and methods, but rather are provided as a representative embodiment and/or arrangement for teaching one skilled in the art one or more ways to implement the methods.

It is to be further understood that like numerals in the drawings represent like elements through the several figures, and that not all components and/or steps described and illustrated with reference to the figures are required for all embodiments or arrangements The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Terms of orientation are used herein merely for purposes of convention and referencing, and are not to be construed as limiting. However, it is recognized these terms could be used with reference to a viewer. Accordingly, no limitations are implied or to be inferred.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A system for inspecting a surface of a structure for defects comprising:
    an inspection apparatus including a heating device for heating a section of the surface of the structure, an infrared camera for receiving infrared radiation from the surface in response to heating, a controller configured to generate thermographs from the received infrared radiation, and a communication device coupled to the controller;
    a training system including an expert system module configured to determine correlations between a set of thermographs, the thermographs generated by a thermal simulation of modeled structural elements with defects, and parameters of the modeled structural elements; and a computer system communicatively coupled to the training system and to the communication device of the inspection apparatus, the computer system adapted to receive thermographs received from the inspection apparatus and to detect quantitative parameters of defects in the structure using the correlations obtained from the training system, wherein the quantitative parameters detected by the computer system include a location, a depth, an orientation, a defect type and an entrapped media type.

2. A system for inspecting a surface of a structure for defects comprising:

an inspection apparatus including a heating device for heating a section of the surface of the structure, an infrared camera for receiving infrared radiation from the surface in response to heating, a controller configured to generate thermographs from the received infrared radiation, and a communication device coupled to the controller;

a training system including an expert system module configured to determine correlations between a set of thermographs, the thermographs generated by a thermal simulation of modeled structural elements with defects, and parameters of the modeled structural elements; and a computer system communicatively coupled to the training system and to the communication device of the inspection apparatus, the computer system adapted to receive thermographs received from the inspection apparatus and to detect quantitative parameters of defects in the structure using the correlations obtained from the training system, wherein parameters of each modeled structural element includes a location, defect type, defect size, defect orientation and entrapped media.

3. The system of claim 2, wherein the defect type is one of delamination, unique void, matrix cracking, fiber-matrix de-bonding, multiple voids, and holes.

4. The system of claim 2, wherein the entrapped media is liquid or gas selected for inspection.

5. A system for inspecting a surface of a structure for defects comprising:

an inspection apparatus including a heating device for heating a section of the surface of the structure, an infrared camera for receiving infrared radiation from the surface in response to heating, a controller configured to generate thermographs from the received infrared radiation, and a communication device coupled to the controller;

a training system including an expert system module configured to determine correlations between a set of thermographs, the thermographs generated by a thermal simulation of modeled structural elements with defects, and parameters of the modeled structural elements; and a computer system communicatively coupled to the training system and to the communication device of the inspection apparatus, the computer system adapted to receive thermographs received from the inspection apparatus and to detect quantitative parameters of defects in the structure using the correlations obtained from the training system, wherein the training system further includes an optimized acquisition parameter module configured to automatically determine acquisition parameters for controlling the inspection apparatus based on material properties of the structure, environmental conditions, and a thermal analysis of a modeled structural element.

6. The system of claim 5, wherein the acquisition parameters determined by the optimized acquisition parameter module include a heating mode, heating time and target heat flux level for operating the heating device, and an acquisition time for operating the infrared camera of the inspection apparatus.

7. The system of claim 5, wherein the thermal analysis is performed on a modeled structural element having at least one of a smallest and a deepest defect.

8. A system for inspecting a surface of a structure for defects comprising:

an inspection apparatus including a heating device for heating a section of the surface of the structure, an infrared camera for receiving infrared radiation from the surface in response to heating, a controller configured to generate thermographs from the received infrared radiation, and a communication device coupled to the controller;

a training system including an expert system module configured to determine correlations between a set of thermographs, the thermographs generated by a thermal simulation of modeled structural elements with defects, and parameters of the modeled structural elements; and a computer system communicatively coupled to the training system and to the communication device of the inspection apparatus, the computer system adapted to receive thermographs received from the inspection apparatus and to detect quantitative parameters of defects in the structure using the correlations obtained from the training system, wherein the computer system receives acquisition parameters from the training system and transmits the acquisition parameters to the inspection apparatus.

9. A system for inspecting a surface of a structure for defects comprising:

an inspection apparatus including a heating device for heating a section of the surface of the structure, an infrared camera for receiving infrared radiation from the surface in response to heating, a controller configured to generate thermographs from the received infrared radiation, and a communication device coupled to the controller;

a training system including an expert system module configured to determine correlations between a set of thermographs, the thermographs generated by a thermal simulation of modeled structural elements with defects, and parameters of the modeled structural elements; and a computer system communicatively coupled to the training system and to the communication device of the inspection apparatus, the computer system adapted to receive thermographs received from the inspection apparatus and to detect quantitative parameters of defects in the structure using the correlations obtained from the training system, wherein the inspection apparatus includes a clamp element for fixing the apparatus to the surface of the structure and a chassis unit for housing the heating element and infrared camera.

10. The system of claim 9, wherein the chassis unit is slidingly coupled to the clamp element and rotatable circumferentially with respect to the surface of the structure.

11. The system of claim 9, wherein the chassis unit and clamp element are coupled to rotatable and translatable wheels enabling the inspection apparatus to rotate circumferentially and translate longitudinally along the surface of the structure.

12. A system for inspecting a surface of a structure for defects comprising:
   an inspection apparatus including a heating device for heating a section of the surface of the structure, an infrared camera for receiving infrared radiation from the surface in response to heating, a controller configured to generate thermographs from the received infrared radiation, and a communication device coupled to the controller;
   a training system including an expert system module configured to determine correlations between a set of thermographs and parameters of modeled structural elements, and an optimized acquisition parameter module configured to automatically determine parameters for controlling the inspection apparatus based on material properties of the structure and environmental conditions; and
   a computer system communicatively coupled to the training system and to the communication device of the inspection apparatus, the computer system adapted to receive thermographs received from the inspection apparatus and to detect quantitative parameters of defects in the structure using the correlations obtained from the training system;
   wherein the quantitative parameters include an entrapped media type.

13. An apparatus for inspecting a surface of a structure for defects comprising:
   a clamp element for removably fixing the apparatus in proximity to the surface of the structure;
   a chassis unit coupled to the clamp element, the chassis unit housing:
      a heating device configurable to heat a section of the surface of the structure;
      an infrared camera configurable to acquire infrared radiation from the surface of the structure;
      a controller communicatively coupled to and operative to control the heating device and infrared camera; and
      a transceiver coupled to the controller;
   wherein the controller receives optimal acquisition parameters from a system that determines the parameters based on a material of the structure and environmental conditions in a proximity of the structure.

14. The inspection apparatus of claim 13, wherein the optimal acquisition parameters include a heating time and target flux level for applying heat the section of the structure using the heating device and an acquisition time detecting infrared radiation from the structure using the infrared camera.

15. The inspection apparatus of claim 13, further comprising sliding elements coupled between the chassis unit and the clamp element, the sliding elements enabling the chassis unit to rotate along the clamp element circumferentially around the structure.

16. The inspection apparatus of claim 13, further comprising rotatable and translatable wheels fixed to ends of the clamp element and chassis unit, the wheels enabling the clamp element and chassis unit to rotate circumferentially and translate longitudinal over the surface of the structure.

* * * * *